(12) United States Patent
Russell et al.

(10) Patent No.: US 6,942,873 B2
(45) Date of Patent: Sep. 13, 2005

(54) MICROFABRICATION OF MEMBRANES CONTAINING PROJECTIONS AND GROOVES FOR GROWING CELLS

(75) Inventors: Brenda Russell, Evanston, IL (US); Tejal A. Desai, Chicago, IL (US); Luke Hanley, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 47 days.

(21) Appl. No.: 09/961,834

(22) Filed: Sep. 24, 2001

(65) Prior Publication Data

US 2002/0081726 A1 Jun. 27, 2002

Related U.S. Application Data

(60) Provisional application No. 60/235,094, filed on Sep. 25, 2000.

(51) Int. Cl.[7] ............................ A61F 2/00; C12N 11/02; C12N 11/08; C12N 5/06; C12N 5/08
(52) U.S. Cl. ...................... 424/426; 424/93.7; 424/423; 424/424; 435/177; 435/180; 435/395; 435/401; 435/402
(58) Field of Search .............................. 435/177, 180, 435/395, 401, 402; 424/423, 424, 426, 93.7

(56) References Cited

U.S. PATENT DOCUMENTS

| | | | |
|---|---|---|---|
| 4,789,601 A | 12/1988 | Banes | 428/447 |
| 4,917,793 A | * 4/1990 | Pitt et al. | 210/94 |
| 5,272,084 A | 12/1993 | O'Connell et al. | 435/240.243 |
| 5,721,131 A | 2/1998 | Rudolph et al. | 435/240.243 |
| 5,733,538 A | 3/1998 | Riffle | 424/78.08 |
| 5,750,103 A | 5/1998 | Cherksey | 424/93.21 |
| 5,800,811 A | 9/1998 | Hall et al. | 424/93.7 |
| 5,804,178 A | 9/1998 | Vacanti et al. | 424/93.7 |
| 5,855,610 A | 1/1999 | Vacanti et al. | 623/11 |
| 5,885,829 A | 3/1999 | Mooney et al. | 435/325 |

FOREIGN PATENT DOCUMENTS

| | | |
|---|---|---|
| CA | 2195867 | 2/1996 |
| WO | WO 96/03094 | 2/1996 |
| WO | WO 97/05238 | 2/1997 |
| WO | WO 99/01538 | 1/1999 |

OTHER PUBLICATIONS

Matsuda et al., "Microfabricated Surface Designs for Cell Culture and Diagnosis", ASAIO Journal, 40 (1994) Jul.—Sep., No. 3, Hagerstown, Maryland, U.S., pp. M594–M597.

Ada et al., "Ion beam modification and patterning of organosilane self–assembled monolayers", *J. Vac. Sci. Technol.*, B 13:2189–2196 (1995).

(Continued)

*Primary Examiner*—David M. Naff
(74) *Attorney, Agent, or Firm*—Marshall, Gerstein & Borun LLP

(57) ABSTRACT

The present invention provides a novel substrate for use in growing cells and for the study of mechanobiology. The membrane of the present invention comprises appropriate microtopography and surface chemical modifications to facilitate the production of adherent and oriented cells that phenotypically resemble cells in vivo.

17 Claims, 16 Drawing Sheets-

OTHER PUBLICATIONS

Anversa et al., "Morphometry of right ventricular hypertrophy induced by strenuous exercise in rat", *Am. J. Physiol.*, 243:H856–H861 (1982).

Bhatia et al., "Microfabrication of Hepatocyte/Fibroblast Co–cultures: Role of Homotypic Cell Interactions", *Biotech. Prog.*, 14:378–387 (1998).

Bowden et al., "The controlled formation of ordered, sinusoidal structures by plasma oxidation of an elastomeric polymer", *Appl. Phys. Lett.*, 75:2557–2559 (1999).

Brunette, "Mechanical Stretching Increases the Number of Epithelial Cells Synthesizing DNA in Culture", *Cell Science*, 69:35–45 (1984).

Bucaro et al., "Photolithography as a Tool to Fabricate Polymeric Flow Chambers for In–Vitro Cellular Applications", *IEEE Conference Transactions*, 0–7803–3869–3/97:217–219 (1997).

Buckley et al., "Osteoblasts increase their rate of division and align in response to cyclic, mechanical tension in vitro", *Bone Miner.*, 4:225–236 (1988).

Byron et al., "Myosin heavy chain turnover in cultured neonatal rat heart cells: effects of $[Ca^{2+}]_i$ and contractile activity", *Am. J. Physiol.*, 271:C1447–C1456 (1996).

Cadre et al., "Cyclic Stretch Down–regulates Calcium Transporter Gene Expression in Neonatal Rat Ventricular Myocytes", *J. Mol. Cell. Cardiol.*, 30:2247–2259 (1998).

Chen et al., "Micropatterned Surfaces for Control of Cell Shape, Position, and Function", *Biotech. Prog.*, 14:356–363 (1998).

Cooper, "Cardiocyte Adaptation to Chronically Altered Load", *Ann. Rev. Physiol.*, 49:501–518 (1987).

Copeland et al., "Transformation of NIH/3T3 Mouse Cells by DNA of Rous Sarcoma Virus", *Cell*, 17:993–1002 (1979).

Desai et al., "Microfabricated Immunoisolating Biocapsules", *Biotechnol. Bioeng.*, 57:118–120 (1998).

Deutsch et al., "Fabrication of Microtextured Membranes for Cardiac Myocyte Attachment and Orientation", *J. Biomed. Mater Res. Applied Biomaterials.* 53:267–275 (2000).

Gerdes et al., "Structural Remodeling of Cardiac Myocytes in Patients with Ischemic Cardiomyopathy", *Circulation*, 86:426–430 (1992).

Eble et al., "Contractile activity is required for sarcomeric assembly in phenylephrine–induced cardiac myocyte hypertrophy", *Am. J. Physiol.*, 274:C1226–C1237 (1998).

Eble et al., "Endothelin–induced cardiac myocyte hypertrophy: role for focal adhesion kinase", *Am. J. Physiol Heart Cir. Physiol.*, 278(5):H1695–H1707 (2000).

Eisenberg et al., "Distribution of Myosin Heavy Chain mRNA in Normal and Hyperthyroid Heart", *J. Mol. Cell Cardiol.*, 23(3):287–296 (1991).

Epstein and Fischman, "Molecular Analysis of Protein Assembly in Muscle Development", *Science*, 251:1039–1044 (1991).

Ferguson et al., "Monolayers on Disordered Substrates: Self–Assembly of Alkyltrichlorosilanes on Surface–Modified Polyethylene and Poly(dimethylsiloxane)", *Macromolecules*, 26:5870–5875 (1993).

Gaits et al., "Increase in receptor–like protein tyrosine phosphatase activity and expression level on density–dependent growth arrest of endothelial cells", *Biochem. J.*, 311:97–103 (1995).

Galiana et al., "Indentification of a neural–specific cDNA, NPDC–1, able to down–regulate cell proliferation and to suppress transformation", *Proc. Nat'l. Acad. Sci. (USA)*, 92:1560–1564 (1995).

Goldspink et al., "Beating affects the posttranscriptional regulation of α–myosin mRNA in cardiac cultures", *Am. J. Physiol.*, 271:H2584–H2590 (1996).

Goldspink et al., "Localization of cardiac α–myosin heavy chain mRNA is regulated by its 3' untranslated region via mechanical activity and translational block", *J. Cell Sci.*, 110:2969–2978 (1997).

Green et al., "Fibroblast response to microtextured silicone surfaces: Texture orientation into or out of the surface", *J. Biomed. Mater. Res.*, 28(5):647–53 (1994).

Harris, "Tissue Culture Cells on Deformable Substrata: Biomechanical Implications", *Journal of Biomechanical Engineering*, 106:19–24 (1984).

Heidkamp and Russell, "Calcium not strain regulates localization of α–myosin heavy chain mRNA in oriented cardiac myocytes", *Cell Tissue Research*, 305:121–127 (2001).

Johnson et al., "Selective tumorigenesis in non–parenchymal liver epithelial cell lines by hepatocyte growth factor transfection", *Cancer Letters*, 96:37–48 (1995).

Koizumi et al., "Turnover Rates of Structural Proteins of Rabbit Skeletal Muscle", *J. Biochem. (Tokyo)*, 76(2):431–439 (1974).

Kuppuswamy et al., "Association of Tyrosine–phosphorylated c–Src with the Cytoskeleton of Hypertrophying Myocardium", *J. Biol. Chem.*, 14:272(7):4500–4508 (1997).

Land et al., "Tumorigenic conversion of primary embryo fibroblasts requires at least two cooperating oncogenes", *Nature*, 304:596–602 (1983).

Lateef et al., "Stretching and Fibroblast Growth on GRGD-SP–Peptide Modified Silicone Membranes", *Amer. Chem. Soc. Polym. Mater. Sci. Engin. Prepr.*, 85:403–404 (2001).

Lieberman et al., "Isolated muscle cells as a physiological model", *Am. J. Physiol.*, 22:C349–C363 (1987).

Lin et al., "Polygons and Adhesion Plaques and the Disassembly and Assembly of Myofibrils in Cardiac Myocytes", *J. Cell Biol.*, 108:2355–2367 (1989).

Low et al., "Nonuniform Rates of Turnover of Myofibrillar Proteins in Rat Diaphragm", *J. Cell Biol.*, 56:590–595 (1973).

Marc Madou, *Fundamentals of Microfabrication*, CRC Press, Baton Rouge, p. 127, 351, 358–359.

Morkin et al., "Comparison of the Synthesis of the Light and Heavy Chains of Adult Skeletal Myosin", *Biochim Biophys Acta*, 324:420–429 (1973).

Olivetti et al., "Apoptosis in the Failing Human Heart", *New England J. Med.*, 336(16):1131–1141 (1997).

Pardo et al., "Vinculin is a Component of an Extensive Network of Myofibril–Sarcolemma Attachment Regions in Cardiac Muscle Fibers", *J. Cell Biol.*, 97:1081–1088 (1983).

Perhonen et al., "Microtubules are Needed for Dispersal of α–myosin Heavy Chain mRNA in Rat Neonatal Cardiac Myocytes", *J. Mol. Cell Cardiol.*, 30:1713–1722 (1998).

Rhee et al., "The Premyofibril: Evidence for its Role in Myofibrillogenesis", *Cell Motil Cytoskeleton*, 28:1–24 (1994).

Russell et al., "Remodeling of myofibrils: subcellular distribution of myosin heavy chain mRNA and protein", *Am. J. Physiol.*, 262:R339–345 (1992).

Samarel and Engelmann, "Contractile activity modulates myosin heavy chain–β expression in neonatal rat heart cells", *Am. J. Physiol.*, 261:H1067–1077 (1991).

Samarel et al., "Contractile arrest accelerates myosin heavy chain degradation in neonatal rat heart cells", *Am. J. Physiol.*, 263:C642–C652 (1992).

Sanger et al., "Myofibrillogenesis in Living Cells Microinjected with Fluorescently Labeled Alpha–Actinin", *J. Cell Biol.*, 102:2053–2066 (1986).

Schmidt and von Recum, "Texturing of polymer surfaces at the cellular level", *Biomaterials*, 12:385–389 (1991).

Schultheiss et al., "Differential Distribution of Subsets of Myofibrillar Proteins in Cardiac Nonstriated and Striated Myofibrils", *J. Cell Biol.*, 110:1159–1172 (1990).

Sharp et al., "Mechanical forces regulate focal adhesion and costamere assembly in cardiac myocytes", *Am. J. Physiol.*, 42:H546–H556 (1997).

Sharp et al., "Contractile Activity Modulates Actin Synthesis and Turnover in Cultured Neonatal Rat Heart Cells", *Circ. Res.*, 73:172–183 (1993).

Simpson et al., "Contractile Activity and Cell–Cell Contact Regulate Myofibrillar Organization in Cultured Cardiac Myocytes", *J. Cell Biol.*, 123:323–336 (1993).

Simpson et al., "Modulation of Cardiac Myocyte Phenotype In Vitro by the Composition and Orientation of the Extracellular Matrix", *J. Cell Physiol.*, 161(1):89–105 (1994).

Simpson et al., "Mechanical regulation of cardiac myocyte protein turnover and myofibrillar structure", *Am. J. Physiol.*, 270:C1075–C1087 (1996).

Strait et al., "Role of protein kinase C–ε in hypertrophy of cultured neonatal rat ventricular myocytes", *Am. J. Physiol Heart Circ. Physiol.*, 280(2):H756–H766 (2001).

Terracio et al., "Effects of Cyclic Mechanical Stimulation of the Cellular Components of the Heart: In Vitro", *In Vitro Cellular & Developmental Biology*, 24:53–58 (1988).

Terracio et al., "Expression of Collagen Binding Integrins During Cardiac Deevelopment and Hypertrophy", *Circ. Res.*, 68:734–744 (1991).

Thompson et al., "Atrophy Reversal and Cardiocyte Redifferentiation in Reloaded Cat Myocardium", *Circ. Res.*, 54:367–377 (1984).

Valyi–Nagy et al., "Spontaneous and Induced Differentiation of Human Melanoma Cells", *Int. J. Cancer*, 54:159–165 (1993).

Vandenburgh, "Mechanical forces and their second messengers in stimulating cell growth In Vitro", *Am. J. Physiol.*, 262:R350–355 (1992).

Vandenburgh et al., "Computer–aided mechanogenesis of skeletal muscle organs from single cells in vitro", *FASEB J.*, 5:2860–2867 (1991).

Velcich et al., "Patterns of Expression of Lineage–specific Markers during the in Vitro–induced Differentiation of HT29 Colon Carcinoma Cells", *Cell Growth Differ.*, 6:749–757 (1995).

Wikman–Coffelt et al., "Studies on the Synthesis and Degradation of Light and Heavy Chains of Cardiac Myosin", *J. Biol. Chem.*, 248:5206–5207 (1973).

Xiao et al., "Covalent Attachment of Cell–Adhesive, (Arg–Gly–Asp)–Containing Peptides to Titanium Surfaces", *Langmuir*, 14:5507–5516 (1998).

Yanaka et al., "Statistical analysis of multiple cracking phenomenon of a $SiO_x$ thin film on a polymer substrate", *J. Appl. Phys.*, 90:713–719 (2001).

Yeoh and Holtzer, "The Effect of Cell Density, Conditioned Medium and Cytosine Arabinoside on Myogenesis in Primary and Secondary Cultures", *Experiment Cell Research*, 104(1):63–78 (1977).

Zak et al., "Comparison of Turnover of Several Myofibrillar Proteins and Critical Evaluation of Double Isotope Method", *J. Biol. Chem.*, 252(10):3430–3435 (1977).

Middleton et al., Synthetic Biodegradable Polymers as Medical Devices, *Medical Plastics and Biomaterials Magazine*, pp. 1–19 (1998).

Rand Issue Paper, *Science and Technology Policy Institute*, pp. iii–61 (2000).

* cited by examiner

Cyclin D1 protein expression in cardiac fibroblasts cultured on flat and pegged silicone membranes

SEQUENCE LISTING

```
<160> NUMBER OF SEQ ID NOS: 6

<210> SEQ ID NO 1
<211> LENGTH: 6
<212> TYPE: PRT
<213> ORGANISM: Fibronectin ligand receptor
```

```
<400> SEQUENCE: 1

Gly Arg Gly Asp Ser Pro
1               5

<210> SEQ ID NO 2
<211> LENGTH: 6
<212> TYPE: PRT
<213> ORGANISM: Laminin ligand receptor

<400> SEQUENCE: 2

Tyr Ile Gly Ser Arg Cys
1               5

<210> SEQ ID NO 3
<211> LENGTH: 15
<212> TYPE: PRT
<213> ORGANISM: Synthetic peptide

<400> SEQUENCE: 3

Cys Gly Gly Glu Gly Tyr Gly Glu Gly Arg Gly Asp Ser Pro Gly
1               5                   10                  15

<210> SEQ ID NO 4
<211> LENGTH: 4
<212> TYPE: PRT
<213> ORGANISM: Synthetic peptide
<220> FEATURE:
<221> NAME/KEY: misc_feature
<222> LOCATION: (1)..(1)
<223> OTHER INFORMATION: X = any amino acid

<400> SEQUENCE: 4

Xaa Arg Gly Asp
1

<210> SEQ ID NO 5
<211> LENGTH: 4
<212> TYPE: PRT
<213> ORGANISM: Synthetic peptide
<220> FEATURE:
<221> NAME/KEY: misc_feature
<222> LOCATION: (4)
<223> OTHER INFORMATION: Xaa = any amino acid

<400> SEQUENCE: 5

Arg Gly Asp Xaa
1

<210> SEQ ID NO 6
<211> LENGTH: 5
<212> TYPE: PRT
<213> ORGANISM: Synthetic peptide
<220> FEATURE:
<221> NAME/KEY: misc_feature
<222> LOCATION: (1)
<223> OTHER INFORMATION: Xaa = any amino acid
<221> NAME/KEY: misc_feature
<222> LOCATION: (5)
<223> OTHER INFORMATION: Xaa = any amino acid

<400> SEQUENCE: 6

Xaa Arg Gly Asp Xaa
1               5
```

MICROFABRICATION OF MEMBRANES CONTAINING PROJECTIONS AND GROOVES FOR GROWING CELLS The present application claims the benefit of priority of U.S. Provisional application No. 60/235,094 filed Sep. 25, 2000. The entire text of that specification is incorporated herein by reference.

FIELD OF THE INVENTION

The present invention relates generally to the field of cell growth and culture. More particularly, the present invention provides novel methods and compositions for the growth of cells in an anatomically correct adult phenotype in vitro.

BACKGROUND

Cells in the body respond to extracellular stimuli, that are both biochemical and mechanical in nature (Vandenburgh, Am. J. Physiol 262:R350–355, 1992; Buckley, Bone Miner. 4:225–236, 1988; Brunette, Cell Science, 69:35–45, 1984; Harris, 3. Biomech Engineering, 106:19–24, 1984). Both endothelium and muscle respond dynamically to mechanical stimuli and serve as signal transduction interfaces. Although a much focused research topic in cell physiology, there are some fundamental issues in experimental set-up of muscle cell cultures which have not been adequately addressed.

Mechanobiological studies usually involve statically strained membranes upon which cell monolayers are grown. However, such in vitro approaches are ineffective at providing a good indication of cell function in vivo for a number of reasons. Firstly, these cell culture systems produce significant detachment between the membrane that is being stretched and the overlying substrata. Secondly, unlike the complex three-dimensional force effects seen in vivo, the traditional in vitro culture systems forces are transmitted in only one direction. Furthermore, the complex three-dimensional arrangement of myocytes, and in particular, cardiac myocytes as found in vivo, is usually lacking in the in vitro models. Therefore, in understanding the role of mechanical stimuli upon cell functional processes in culture, it would be beneficial to provide an appropriate membrane or matrix that will more closely mimic the in vivo cellular arrangement.

An example of this can be seen in studies examining the effects of stretch on cardiac gene regulation. In such experiments, myocytes, usually rat cardiac myocytes, are grown in monolayer culture upon silicone and subjected to external mechanical stress. There have been studies of cardiac myocytes, in which the rate of protein synthesis for non-aligned cells has been measured using silicone membranes that used collagen to keep cells attached. (Terracio et al., In Vitro Cellular and Developmental Biology, Vol. 24, 1988; Sharp et al., Circ. Res. 73: 172–183,1993; Am. J. Physiol, 42: H546–556, 1997). However, even though myocytes do adhere to collagen quite well in static culture, there are still significant problems with detachment of the collagen layer from the silicone substrate upon repeated mechanical deformation. It is not surprising that this occurs, especially since it is well established that proteins and cells do not exhibit good adherence to smooth, low surface energy materials such as silicone.

To date, primary neonatal cultures have been the mainstay in the study of myocyte function since contractile cardiac cell lines are not available. However, when it comes to the study of the contractile function and processes of assembly primary neonatal cells are woefully inadequate since they generally have very few functioning myofibrils. Contractile activity is clearly an important signal in regulation of myocyte cell shape that leads, in turn, to remodeling the shape and function of the whole heart. Unfortunately, most adult and neonatal myocyte culture systems display little or no contractile activity.

Thus, there is a need for phenotypically normal myocytes that can be manipulated experimentally. Furthermore there is a need to develop a culture substrata that allows cells to adhere and remain adhered during the application of mechanical and other force.

SUMMARY OF THE INVENTION

The present invention provides a novel substrata for use in growing cells. The membrane of the present invention comprises appropriate microtopography and surface modifications to facilitate the production of adherent and oriented cells that phenotypically resemble cells in vivo. Particularly preferred for the present invention are muscle cells.

Specifically, the present invention contemplates a biocompatible, deformable membrane for the growth of cells e.g., muscle cells, comprising a microtextured polymer membrane having projections of between about 1 $\mu$m to about 100 $\mu$m in size and longitudinal grooves; wherein the polymer membrane comprises a surface modification to facilitate cellular adhesion to the membrane, and further wherein the growth of the cells on the membrane provides enhanced cellular differentiation of the cells as compared to growth on the polymer membrane in the absence of the grooves and/or the pegs.

Specifically contemplated are microtextured polymer membrane having projections may be about 1 $\mu$m, about 2 $\mu$m, about 3 $\mu$m, about 4 $\mu$m, about 5 $\mu$m, about 6 $\mu$m, about 7 $\mu$m, about 8 $\mu$m, about 9 $\mu$m, about 10 $\mu$m, about 11 $\mu$m, about 12 $\mu$m, about 13 $\mu$m, about 14 $\mu$m, about 15 $\mu$m, about 16 $\mu$m, about 17 $\mu$m, about 18 $\mu$m, about 19 $\mu$m, about 20 $\mu$m, about 22 $\mu$m, about 24 $\mu$m, about 26 $\mu$m, about 28 $\mu$m, about 30 $\mu$m, about 32 $\mu$m, about 34 $\mu$m, about 36 $\mu$m, about 38 $\mu$m, about 40 $\mu$m, about 42 $\mu$m, about 44 $\mu$m, about 46 $\mu$m, about 48 $\mu$m, about 50 $\mu$m, about 52 $\mu$m, about 54 $\mu$m, about 56 $\mu$m, about 58 $\mu$m, about 60 $\mu$m, about 62 $\mu$m, about 64 $\mu$m, about 66 $\mu$m, about 68 $\mu$m, about 70 $\mu$m, about 72 $\mu$m, about 74 $\mu$m, about 76 $\mu$m, about 78 $\mu$m, about 80 $\mu$m, about 82 $\mu$m, about 84 $\mu$m, about 86 $\mu$m, about 88 $\mu$m, about 90 $\mu$m, about 92 $\mu$m, about 94 $\mu$m, about 96 $\mu$m, about 98 $\mu$m, and about 100 $\mu$m. "Size" encompasses any of the dimensions of a projection including the height (or depth in the event that the projection is an inverted projection) of the projection from the base planar level of the membrane, the diameter of the projection or the width of the projection. The length of the projection may be 5 cm (50,000 $\mu$m) or more and may span the entire length of the wafer. Any combination of these sizes for a given projection can have any combination of the measurements of the exemplary values listed above.

The preferred size employed in any given culture system will depend on the cell type being grown on the membrane. For example, for the growth of fibroblasts, one of skill in the art would find it desirable to employ membranes with projections in the lower end of the range, such as for example projections of about 2 $\mu$M to about 5 $\mu$M in size. For adult cardiac cells, one would preferably select membranes that have mid-sized projections such as e.g., about 50 $\mu$M in size. Membranes having larger projections e.g., 100 $\mu$M in size would be better for growing adult skeletal muscle cells. Of course, these measurements and cells sizes are merely exemplary and those of skill in the art will understand that the length and diameter of cell types can vary from a few microns to several hundred microns in size. Given the method and compositions described herein, those of skill in the art should be able to produce and employ the membranes of the invention to fit varying cells types and sizes. Also it should be noted that not only the size but the spacing of the projections also may be varied.

A variety of shapes and forms are intended to be encompassed by the term "projection." Such a projection may be one which protrudes out of and above the surface of the membrane. Alternatively, a projection may be one that is configured inwards from the surface of the membrane so as to produce a dimple or indentation in the membrane. The shape of the projection may be regular or irregular and the projections may be regularly or irregularly positioned on the surface of the membrane. The shape of the projections may be for example, conical, pyramid shaped, cylindrical, globular, rectangular or may be a heterogeneous mix of shapes. The membrane may be arranged and shaped in any format commonly used for culturing cells or indeed any shape that may be conducive to allowing a particular cell culture to grow in mass that mimics its in vivo organ growth. The membrane may be planar, tubular, spherical, configured as a disk or stacked.

The membranes of the present invention are biocompatible. The term biocompatible as used herein generally refers to membranes which are non-toxic, chemically inert, and substantially non-immunogenic when used internally in the patient and which are substantially insoluble in blood or other bodily fluids. The term biocompatible is one that is generally understood by those of skill in the art and has been defined by the National Institutes of Health to encompass any substance that may be placed in intimate contact with biological components without harmful effects. In addition to being biocompatible, the membranes of the present invention also have the desirable property of being deformable. The term "deformable" as used herein is intended to mean that the membranes have the ability to be mechanically deformed without loss of integrity of the surface microtopography or the surface chemical modification. The deformable membrane is such that it can withstand the physiological range of stress/strain that the cells being cultured on the membrane experience in vivo. For example, a heart cell experiences extension of length changes that stretch the cell to +/−20% of its resting size. Additionally the cell experiences a number of beats/minute and a pulsatile pressure from blood flow. A membrane for growing myocytes should preferably be able to withstand the application of such extreme forces. On the other hand, bone cells for bone regeneration cannot withstand such pressures and/or forces and the membranes for the growth of such cells need not be as resilient as those used for growth of myocytes.

The chemical modifications of the membranes are resistant to deterioration upon application of mechanical stress. By "resistant to deterioration," it is meant that the surface modification does not readily fall off or become detached, degrade, undergo slippage, become removed or otherwise be cleaved from the surface of the membranes of the present invention as compared to other non-deformable membranes.

The polymer material may be any polymer conventionally employed for cell culture and may be for example selected from the group consisting of silicone, or other elastomeric polymers, hydrogels, biodegradables, bioerodible. Surface modifications contemplated to be useful are those that allow for attachment of cells to the surface of the membrane, for example, through providing ligands for receptors that may be present in the cell surface of the cell to be cultured. The invention particularly contemplates surface modifications, which comprise attachment of laminin or fibronectin to the membrane, or partial peptide sequences of laminin or fibronectin or modification of laminin or fibronectin which nevertheless allow the laminin or fibronectin to act as a surface modification for the attachment of cells. Growth of the muscle cells on the membranes of the present invention produces muscle cells that have contractile function and/or the cells have mechanical deformation properties that are similar to the mechanical deformation properties of said cells in vivo.

Also provided is a cell culture model for the growth and development of muscle cells comprising a membrane for the growth of cells comprising a microtextured polymer membrane having projections of between about 1 $\mu$m to about 100 $\mu$m in size and longitudinal grooves; wherein the polymer membrane comprises a surface modification to facilitate cellular adhesion to the membrane, wherein the membrane comprises surface microtopography to facilitate cellular orientation; and further wherein the growth of the cells on the membrane provides enhanced cellular differentiation of the cells as compared to growth on the polymer membrane in the absence of the grooves and pegs.

Other aspects of the invention contemplate methods of growing e.g., muscle cells comprising contacting the cells with the membrane of the present invention, under media conditions suitable to facilitate the growth of the cell wherein growth of the cells on the membrane reproduces the physiological micro-architecture of the cells. More particularly, the cells may be muscle cells and even more particularly, the cells may be myocardial cells. It is contemplated that the muscle and other cells grown on the membrane are responsive to neurohormonal stimulation. In alternative embodiments, it is contemplated that the muscle cells grown on the membrane exhibit contractile function that mimic the contractile function of the muscle cell in vivo.

Also provided is a method of organogenesis comprising providing cells; contacting the cells with the membrane of the present invention; growing the cell in culture to allow the formation of tissue. In preferred aspects the membrane is a biocompatible membrane. In specific embodiments it is contemplated that the cells may be selected from other cell groups such as skeletal muscle, smooth muscle, cardiac muscle, vascular endothelial cells, lymphatic endothelial cells, stem cells, endothelial cartilage, bone cells or other cell types stimulated by mechanical force or subject to contact inhibition.

Other aspects, features and advantages of the present invention will be apparent from the entirety of the application, including the drawings and detailed description, and all such features are intended as aspects of the invention. Likewise, features of the invention described herein can be recombined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

Also, it should be understood that the detailed description presented below, while providing preferred embodiments of the invention, is intended to be illustrative only since changes and modification within the scope of the invention will be possible whilst still providing an embodiment that is within the spirit of the invention as a whole.

BRIEF DESCRIPTION OF THE DRAWINGS

The following drawing forms part of the present specification and is included to further demonstrate aspects of the present invention. The invention may be better understood by reference to the drawing in combination with the detailed description of the specific embodiments presented herein.

FIG. 3 shows cardiac attachment to micro-pegs (P) and intercalated disc.

FIG. 6 shows cell nucleus and myofibrillar architecture at micro-pegs (P), and cell height.

FIG. 10A shows Mel-1 cells. FIG. 10B shows Mel-1 cells. FIG. 10C shows Mum-2 cells. FIG. 10D shows Mum-2 cells.

DETAILED DESCRIPTION OF THE PREFERRED EMBODIMENTS

Figure 1:
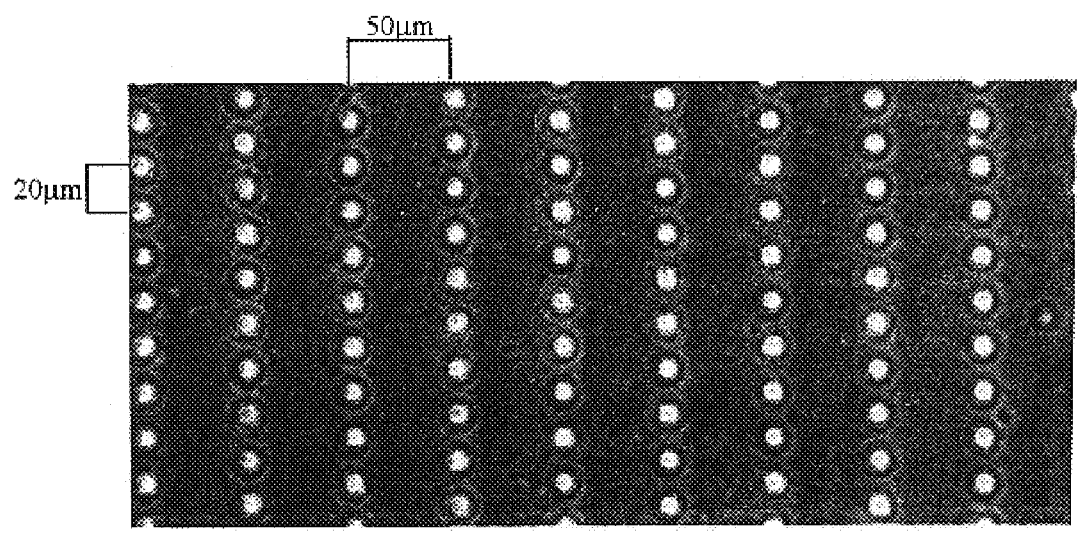
FIG. 1 shows micro-pegged silicone membrane of the present invention viewed with phase microscopy.

The present invention is directed to a novel cell culture system to study the process of myocyte remodeling in vitro which maintains a differentiated in vivo myocyte cell phenotype. The culture system of the present invention, created by microfabrication technology coupled with surface chemistry, allows cells to be grown which more closely mimic in vivo heart physiology. Further, the new culture system yields cells which are responsive to both mechanical and neurohormonal stimuli that are operative in the intact, failing heart in vivo.

In one of the preferred aspects of the present invention, membranes are provided for the growth of muscle cells such that myocytes grown on these membranes obtain the physiological micro-architecture of myocyte cells seen in vivo. In order to produce the membranes, microtextured pegs of varied height are used to generate a polymeric membrane to maximize perpendicular surface for attachment of myoctyes or other cell types thereby permitting force transmission to the myocytes or other cell types in culture that mimics the force transmission experienced by myocytes or other cell types in vivo. Secondly, microtextured grooves of varied length and depth are used to increase cell alignment and circumferential attachment resembling the costameric structural composition for lateral force transmission to the muscle cells in culture. Thirdly, microtextured pegs and grooves are used to simultaneously promote attachment and alignment of myocytes on the polymer membranes with the desired elastomeric, optical, chemical, and biocompatible properties of such cells in vivo.

In addition to providing membranes that promote the appropriate physiological micro-architecture of the myocytes in culture, the present invention further modifies the membranes to alter the surface chemistry of microtextured membrane to promote attachment, adhesion-dependent cell signaling and growth of the cardiomyocytes in culture. More particularly, receptor ligands are attached to the surface of the membranes to facilitate the cellular adhesion. In preferred embodiments, the fibronectin receptor ligand GRGDSP (SEQ ID NO:1) and/or the laminin receptor ligand YIGSRC (SEQ ID NO:2) are covalently bound to the surfaces of the membrane.

The novel, microtextured, adhesive membranes of the present invention allow aligned, anatomically correct adult-phenotype myocytes to form in vitro. Typically, these cardiac myocytes are more "muscular" and can be used to study cardiac adaptive and patho-physiological processes in vitro without the complexity introduced by whole animal sequella to altered cardiac output. The significance of this in vitro model is that growth of fully functional cells on substrata is an essential step in the path towards heart organogenesis and cardiac tissue engineering. Furthermore, the culture systems of the present invention can provide an in vitro model of cardiac cells in progression to heart failure and for remedies and reversal of such undesirable outcomes. While the present invention generally discusses myocytes in culture, it should be understood that the membranes of the present invention also will be useful for the study of mechanobiology of other cell types known to respond to load, such as, for example, bone, connective tissues, endothelial cells (e.g., vascular endothelial cells and lymphatic endothelial cells), stem cells, smooth and skeletal muscle. Of particular interest, the inventors have demonstrated that cancer cells can be grown on the membranes of the present invention to mimic their in vivo, tumor growth behavior.

The membranes of the present invention provide a transparent, biocompatible surface with specific microarchitectures upon which cells exhibit enhanced cellular adhesion due to increased surface area, three dimensional geometries that mimic the in vivo geometric myocyte environment and biocompatible attachment moieties. The microtopography provides anisotropic or directional growth for cells and thus can recreate tissue architecture at the cellular and subcellular level.

Thus, production of fully functional myocytes is facilitated by a three-dimensional membrane which provides a greater surface area for protein attachment, and consequently, for the adherence of cells being cultured. As a result of the three-dimensionality of the membrane, muscle cells continue to actively grow, in contrast to cells in monolayer cultures, which grow to confluence, exhibit contact inhibition, and cease to grow and divide. The three-dimensional membrane allows for a spatial distribution of cellular elements which is more analogous to that found in the counterpart tissue in vivo. The increase in potential volume for muscle cell growth in the three-dimensional system may allow the establishment of localized microenvironments conducive to cellular maturation. It has been recognized that maintenance of a differentiated cellular phenotype requires not only growth/differentiation factors but also the appropriate cellular interactions. The present invention effectively recreates the tissue microenvironment. Details of the methods and compositions for the growth of muscle cells in vitro according to the present invention are presented herein below.

I. Mycocardial Cells and Myocardial Contraction

To the extent that the present invention is directed, in preferred embodiments, to the growth and differentiation of cardiomyocytes in culture, the present section provides a discussion of cardiac cell biology and the contractile properties of muscle cells.

When the heart grows bigger, individual myocytes get larger in size (Zak, Raven Press New York, 1984; Gerdes et al., *Circulation* 86, 426–30, 1992) but probably not greater in number (Olivetti et al., *N Engl J Med.* 17;336(16): 1131–41; 1997). Thus, control of individual cell growth is an important factor for increasing the strength of the heart. An adult myocyte can hypertrophy in volume either by increasing the number of sarcomeres in length and/or the number of myofibrils in cross sectional area. The direction in which the cell grows has major clinical consequences for the mechanical output from the whole heart (Katz, Raven Press, New York 1992). In concentric hypertrophy, the heart wall is thick and cells have a large cross-sectional area while in eccentric hypertrophy the heart wall is thin and the cells are longer than normal (Anversa et al., *Am J. Physiol.* 243 :H856—H861.1982; Gerdes et al., *Circulation* 86, 426–30, 1992). Although there is much descriptive data on the ability of the cells to control their shape in response to load (Thompson et al., *Circ. Res.* 54:367–377, 1984; Cooper, *Ann Rev. Physiol.* 49:501–518, 1987), little is known about the regulation of these growth processes.

Although there is a significant amount of information available regarding the overall processes of transcription, translation and protein degradation in hypertrophy, there has been a lack of adequate culture systems to study mechanical signal transduction and assembly of contractile units (myofibrils) up until the present invention have not been addressed. The inventors contemplate that mechanical strain and neurohormonal stimulation are the primary physiological signals that control myofibril assembly and the net protein accumulation that accounts for cell shape changes. The cell culture system of the present invention provides the first mechanism for investigating the effects of such stimulation on myocytes.

The myofibril is the biological unit of contraction. In muscle, assembly of the sarcomeric proteins into highly organized myofibrils is an ordered and complex process. Formation of the first myofibril (myofibrillogenesis) is the process by which sarcomeres are assembled by bundling of the thick and thin filaments (Epstein and Fischman, *Science* 251, 1039–44, 1991). A future striated muscle starts by looking more like a fibroblast or smooth muscle cell with actin stress cables anchored at the membrane and interspersed with dense Z-bodies. Much of this information has been attained by employing immunochemistry or by introduction of green fluorescent protein (GFP) labeled proteins that can be visualized in living cells (Sanger et al., *J Cell Biol* 102, 2053–66, 1986; Dabiri et al., 1997). It is contemplated that such techniques will be useful in the present invention to determine the physiological micro-architecture and contractile function of the myocytes grown according to the present invention.

Myofibrils in cultured cardiac myocytes form outwards from focal adhesions (Lin et al., *J Cell Biol* 108,2355–67, 1989; Schultheiss et al., *J Cell Biol* 110, 1159–72, 1990), where cells attach to the extracellular matrix via integrins. Terracio et al. (*Circ. Res.* 68:734–744, 1991) first demonstrated the presence of integrins on the cell surface of freshly isolated adult, and cultured neonatal cardiac muscle cells. These transmembrane cell surface receptors connect ECM components (collagens, laminin, fibronectin) to cytoskeletal elements within the cytoplasm of individual myocytes.

In the intact adult muscle, the attachment sites are found around the circumference at the Z-line (costameres) providing a direct link for the transmission of mechanical forces externally to do useful work in pumping blood. In cultured cells, the integrins and attachment sites re-form only at the cell-substratum interface. In both cases, internal forces are transmitted throughout the cytoskeleton and perhaps even to the nucleus (Pardo et al, *J Cell Biol* 97:1081–1088, 1983). Cardiac myocyte integrins are of the β1-type with several different α-subunits. These heterodimeric complexes provide intracellular binding sites for cytoskeletal proteins (vinculin, paxillin, tensin, talin, α-actinin, dystrophin, etc.) which are localized to the cytoplasmic face of the costamere or focal adhesion. These non sarcomeric cytoskeletal proteins thus physically link integrins to sarcomeric actin filaments that terminate at or near these sites. In addition to their structural role, cardiac myocyte focal adhesions and costameres may also be major sites of mechanochemical signal transduction during myocyte remodeling, as their organization appears to be highly regulated by externally applied or intrinsically generated mechanical load (Simpson et al., *J Cell Biol* 123:323–336, 1993; Sharp et al., *Am. J. Physiol,* 42: H546–H556, 1997, Eble et al., *Am J Physiol*

Heart Circ Physiol., 278(5):H1695–H1707, 2000). The role of the costameres and focal adhesions during addition of new filaments to existing myofibrils in hypertrophying cardiomyocytes is presently unclear, but may now be addressed given that the present invention for the first time provides cell culture systems for the study of such a role.

There is a constant turnover of proteins of the contractile units in cardiac myocytes (Low et al., *J Cell Biol* 56, 590–5, 1973; Morkin et al., *Biochim Biophys Acta* 324, 420–9, 1973; Wikman-Coffelt et al., *J Biol Chem* 248, 5206–7, 1973; Koizumi et al., *J Biochem* (Tokyo), 76(2): p. 431–9, 1974; Zak et al., *J Biol Chem.* 252(10): p. 3430–5, 1977). In order to understand such replacement at the level of the contractile machinery, contractile proteins have been labeled and followed (Eisenberg et al., *J Mol Cell Cardiol.* 23(3): p. 287–96, 1991; Russell et al., *Am J Physiol* 262, R339–45, 1992; Rhee et al., *Cell Motil Cytoskeleton* 28, 1–24, 1994). Contractile proteins in vivo are among the longest lived of known proteins. For example, the myosin heavy chain, MyHC, turns over with a half-life of 7–10 days, whereas sarcomeric actin's half-life is approximately 20 days. Sarcomeric protein half-lives vary with age, and are influenced by the hemodynamic load placed upon the muscle cell.

The effects of mechanical load on contractile protein synthesis and degradation have also been studied in vitro, despite shortcomings in the model system of randomly oriented cardiomyocytes maintained in 2-D culture. For instance, it has been demonstrated that inhibition of contractile activity by blockade of calcium transients or inhibition of actin-myosin crossbridge cycling reduces the MyHC and actin content of cultured cells, and leads to a time-dependent disappearance of intact sarcomeres. These effects are entirely reversible, and result from both a decrease in MyHC and actin synthesis, and an increase in the rate of MyHC and actin degradation (Samarel et al., *Am J Physiol* 263, C642–52, 1992; Sharp et al., *Circ.Res.* 73: 172–183, 1993; Byron et al., *Am J Physiol* 271, C01447–56, 1996). Furthermore, static stretch of randomly oriented, 2-D cultures of neonatal myocytes partially suppressed the accelerated degradation of sarcomeric proteins in contractile-arrested cells (Simpson et al., *Am J Physiol* 270, C1075–87, 1996). Stretch also causes MyHC and actin accumulation in contracting cells, again due to both an increase in the rate of protein synthesis and a reduction in the rate of degradation.

The signal transduction pathways responsible for load-induced alterations in contractile protein synthesis and turnover are not known, but are the subject of current, intense investigation. Interest in these processes relates to the fact that abnormal growth and remodeling of cardiac muscle accompanies many common cardiac diseases, and is an independent risk factor for cardiac morbidity and mortality. Nevertheless, understanding of these highly regulated events remains limited, due to the lack of physiologically relevant cell culture models wherein mechanical loading is applied to properly oriented, 3-D cultures with appropriate ECM-cell attachments. The present invention provides such a culture system for the first time. Using this system it is now possible to mechanically deform cardiac cells attached on chemically-bonded, microtextured surfaces prepared by the present invention in order to observe the morphology, growth and gene expression in static versus cyclic stretched myocytes on microtextured membranes.

II. Microfabrication of Membranes

The techniques of microfabrication and micromachining have been recently used to create precisely controlled biomaterial surfaces via photopatterning and etching (Desai et al., *Biotechnol Bioeng* 57:118–120, 1998; Bhatia et al, *Biotech. Prog.* 14:378–387, 1998; Chen et al., *Biotech Prog.* 14:356–363, 1998). Microfabricated substrates can provide unique advantages over traditional biomaterials due to their ability to control surface microarchitecture, topography, and feature size in the nanometer and micron size scale, and control of surface chemistry in a precise manner through biochemical coupling or photopatterning processes. With the capability to design components spanning from the millimeter down to the nanometer range, few other engineering technologies can so closely parallel the microdimensional scale of living cells and tissues.

Traditionally, microfabrication has only been applied to semiconductor materials due to their oxidation and etching properties, using expensive microfabrication equipment. Recently, however, techniques to translate micromachined structures from inorganic to organic polymeric materials have been introduced (Schmidt and von Recum, *Biomaterials,* 12: 385–389, 1991; Bucaro et al, *IEEE Conference Transactions* 0-7803-3869-3/97:217–219, 1997). This opens up unique opportunities in biological and tissue engineering applications. One of the challenges in tissue engineering is to find a more suitable method for the fabrication of scaffolds of defined architecture to guide cell growth and development and to understand what exact factors guide that growth and development. Several polymer processing methods are currently used, including solvent casting, fiber bonding, and membrane lamination. The disadvantage of these techniques lies in the fact that architecture is achieved by altering solute or solvent concentration, thus making it difficult to attain precise reproducible features in the micro- and nano-meter range.

The ability to spatially localize and control interactions of cell types on polymeric materials presents an opportunity to engineer hierarchically and more physiologically correct tissue analogs for mechanical, biochemical, and functional testing. The arrangement of cells in more complex two and three dimensional arrangements has beneficial effects on cell differentiation, maintenance, and functional longevity. For instance, MyHC is 12–15% of the total protein content of the neonatal myocardium in vivo, but only 4–6% in randomly oriented, 2D cultures of spontaneously beating neonatal myocytes. MyHC content decreases even more in contractile-arrested cells. Particularly in studies involving translation of mechanical stimuli via substrate cycling or stretching to cells, it is important to ensure cellular orientation and substrate attachment. The present invention provides membrane substrata for facilitating this objective.

The membranes of the present invention provide a transparent biocompatible surface with specific microarchitectures upon which myocytes can be grown. In an exemplary procedure the microtextured membranes are prepared using silicone membranes. Starting with a clean silicon wafer, a 5 $\mu$m conformal layer of light sensitive photoresist (Michrochem SU8-5, Michrochem Corp., Newton, Mass.) is spun onto the wafer at 1500 RPM for 30 seconds and soft baked at 90° for 6 minutes. A photomask is used to define the pattern on to the photoresist layer upon exposure to UV light. Arrays of 10 by 10 by 10 micron (L×W×H) pegs (with spacing 30 $\mu$M center to center by 100 $\mu$M center to center) are thus photolithographically defined. These dimensions correspond to cell dimension, as myoctyes in culture are typically 50 microns in length and 10–15 microns in diameter. The resulting photoresist structure is developed and hard baked. Subsequently, the surface is spray coated or dipped into adhesion demoter and a thin layer of parylene is deposited on the photoresist/silicon substrate. The parylene deposition layer is approximately 25 microns in thickness.

The parylene layer forms a flexible mold for the elastomeric silicone. Subsequently, silicone (polydimethysiloxane), which is prepared by mixing elastomer and catalyst (A103 Factor II Inc.) in a 10:1 ratio, is deposited on top of the parylene mold and allowed to cure at room temperature for 24–48 hours. The silicone can then be peeled off the parylene and cut to the desired shape and size.

The process for creating microgrooves is similar to the above process for creating micropegs except that a positive phostoresist is used. Shipley 1818 photoresist is spun on the wafer at 500 RPM for 180 seconds. After a 5 minute soft bake the wafer is patterned with a mask aligner for 13 seconds at 20 mW. This results in longitudinal grooves of 5 micron depth. The width and spacing of the grooves can be adjusted as desired according to the mask. The wafer is placed in developer (351 Shipley) for 0.9 minutes with continuous motion and rinsed with deionized water. The purpose of the longitudinal grooves is to orient the myocytes and also to provide a greater surface area for lateral attachment.

It should be understood that given the teachings of the present invention it will be possible for those of skill in the art to produce arrays that correspond to dimensions smaller or larger than those exemplified here and still produce a membrane that will be useful for the growth of cells that bear load.

As indicated elsewhere in the specification, most of the observations to date presented have come from two-dimensional cultured muscle. This is a limiting system in that the myofibrils can only make costameres (attachments) on the bottom surface of the dish and lack the fascia adherens at the ends of the cells. Cultured myocytes at present are (1) not oriented, (2) weakly adherent, and (3) not three-dimensional. The myocytes lack an important third dimension through which useful force is transmitted to the external world surrounding the cell. Early studies have shown that myocytes grow in more physiological arrangements (i.e. muscle-like configurations) when attached to perpendicular, rather than parallel, surfaces created by a pin impaled in a soft dish (Yeoh and Holtzer, *Experimental Cell Research*, 104(1):63–78, 1977) or by Vandenburgh's less well known horizontal device (Vandenburgh et al., *FASEB J.* 5;2860–2867, 1991). The methods for introducing microtopography into the membrane surfaces as presented herein will overcome these architectural defects in cardiac cell anatomy and physiology.

The dimensions of the topographic features on which the cells grow will be modified to correspond to cell dimensions (typically 10–50 µm size range). These platforms will provide a transparent biocompatible surface with specific micro-architectures upon which it is hypothesized cells will exhibit enhanced cellular adhesion. The microtopography provides anisotropic or directional growth for cells and thus, can recreate tissue architecture at the cellular and subcellular level in a reproducible fashion.

For all experimental conditions in Example 2, unmodified (flat) and modified (textured) substrates are placed into culture dishes and seeded with appropriate cells. The effect of surface microarchitecture on cellular attachment and morphology is quantified by image analysis. Cells are fixed with 2% paraformaldehyde and proteins localized using various antibodies (Terracio et al., *In Vitro Cellular and Developmental Biology.* Vol. 24, 1988) to examine morphology under epifluorescent microscopy. Fixed samples also may be studied under SEM to observe interfacial properties. Total protein, DNA and myosin content also may be assessed by standard methods. Details of the immunochemistry and other methods are given in Example 1.

Use of Microtextured Pegs of Varied Height to Maximize Perpendicular Surface for Attachment Permitting Force Transmission as in vivo The perpendicular surface of the membrane may be optimized for cellular attachment. Immunolocalization can then be used to view contractile and focal adhesion proteins. Further, attachment may be assessed by cell density, total protein per DNA, and myosin to total protein ratios.

The silicone membranes with microtextured pegs of varied height optimize adherence and mimic a three-dimensional in vivo environment. Preferably, the membranes are thin (approx. 250 µm) with surface topologies consisting of small finger-like projections (pegs). Preferably, peg heights are 5 to 30 µm to cover the size range of cardiac myocyte height in vivo.

A quantitative epifluorescent and phase light microscopy may be used to anatomically characterize the cells from cell culture; however, a confocal microscope is needed to provide the three-dimensional structure. Confocal microscopy enables one of skill in the art to view three planes for analysis: the conventional view from above the dish as the X-Y plane, the longitudinal Z-Y plane, and the transverse Z-X plane. It has been previously shown that myofibrils only form on the bottom surface of muscle cells in culture (Eisenberg, *Am. J. Physiol.* 22; C349–C363, 1987). This can now be viewed with rhodamine phalloidin in conjunction with DAPI stain which serves to contrast the nucleus. The nature of the cell's attachment in the perpendicular plane between the vertical peg and the myocyte also can be examined through the visualization of focal adhesion proteins.

The degree of attachment of cells on microtextured surfaces and flat membranes is determined, and focal adhesions, cell shape, and myofibrils may be viewed. Attachment is assessed by cell density, total protein per DNA, and myosin to total protein ratios. The morphologic parameters that can be measured are cell surface area, cell perimeter, maximum cell length, and position of cell with respect to the texture. The myofibril height above the bottom of the cell is an index of three dimensionality. In traditional flat surfaces, myofibrils of half micron diameter are stacked only a few cells high. The inventors believe that the peg height allows a significant increase in the stacking of myofibrils. Therefore, confocal microscopy is used to measure the myofibril height in the Z-axis both at the nuclear location and close to the peg. The lateral attachment of myocytes to the pegs is assessed by counting randomly selected areas for the % myocytes attached to a peg. This is compared with the % of cells on flat culture dishes attached to virtual pegs drawn on the photographs after images are captured as described in Example 2.

Use of Microtextured Grooves of Varied Depth to Increase Cell Alignment and Circumferential Attachment Resembling the Costameric Structural Composition.

It is necessary to have parallel aligned myocytes for the mechanical experiments. The purpose of the longitudinal grooves is to orient the myocytes. Grooves should have a cross sectional area that will encompass the cell. A 10 µm×10 µm cross-section may be used however a 20 µm×20 µm also may be used if the cells do not settle into the smaller groove. The height of the groove can be changed according to the height required using the same mask by deeper etching. A positive photoresist is used to create microgrooves in the silicon membrane. The unmasked areas of a positive photoresist are preserved upon exposure to light yielding the grooves of specified dimension in the spun-on photoresist.

The next factor to be considered is how closely the grooves should be spaced laterally. Cells in the animal are polarized, oriented, cylindrical shapes with diameters of 10–15 μm. They are closely packed with intervening connective tissue of a few microns. If the space between the grooves is more than 30 μm, the myocardial cells in between the grooves become randomly oriented. This lateral spacing variable may be determined efficiently using several masks of different groove cross-section area and of different lateral spacing. For example, one of skill in the art can start with three different masks e.g., with 15 μm, 20 μm, and 30 μm laterally. In this manner the influence of spacing on orientation may be determined. Groove length should exceed the 50 μm cell length and may be up to an inch or more.

The degree of attachment and alignment of cells on microtextured and flat membranes can be determined. Alignment is determined stereologically as described in the methods in Example 1. Confocal microscopy is used to observe costameric formations circumferentially in the three-dimensional cell culture system as compared to two-dimensional flat membrane. To do this, the inventors use the conventional view from above the dish as the X-Y plane, the longitudinal Z-Y plane, and the transverse Z-X plane.

Use of a Combination of Microtextured Pegs and Grooves to Simultaneously Promote Attachment and Alignment on Polymer Membranes with Desired Elastomeric, Optical, Chemical, and Biocompatible Properties.

Once optimal groove and peg dimensions for cellular attachment and alignment have been determined, a combination of two masks is used to create the pegs and grooves on the same membrane. This allows exploration of the combined effect of attachment and orientation on cell geometry and size.

In addition, several biomaterials may be used to see if there is any difference in cellular attachment with different materials. Three different polymers are particularly contemplated: polydimethyl siloxane (siloxane), Polylactic/glycolic acid (PLA/PGA), and polyhydroxyethlmethacrylate (PHEMA). These represent the following polymer classes: an elastomer, biodegradable polymer, and hydrogel, respectively. It should be understood that other elastomers, biodegradeable polymers and hydrogels also may be used in place or together with those exemplified herein. The use of biocompatible materials in microfabrication processing is an important step for application of this technology in biology.

Observations of the textured surfaces use phase microscopy. Microscopy is used to verify that the membranes produced are indeed the desired patterns and texture specified. Profilometry is used to measure feature height and depth.

The development of cell culture platforms based on novel three dimensional cellular arrangements as provided by the present invention will provide insight into cell-material interactions for the development of improved in vitro cell culture matrices for investigation into cellular mechanobiology. It is envisioned that the incorporation of microtexturing in such a platform will further facilitate the co-culture and maintenance of differentiated cell states.

Through its ability to achieve highly controlled micro architectures on size scales relevant to living systems (from microns to nanometers), microfabrication technology offers unique opportunities to engineer new tissue models for the investigation of biological phenomena. Microfabricated constructs comprised of specific cell types may be preferred because of their greater relevance to physiological tissue. The ability to spatially localize and control interactions of several cell types on polymeric materials (elastomers, and hydrogels) presents an opportunity to engineer hierarchically and more physiologically correct tissue analogs. The arrangement of multiple cell types in two- and three-dimensional arrangements has beneficial effects on cell differentiation, maintenance, and functional longevity. Additionally, microfabrication can be used not only to create more complex substrates, but also understand fundamental processes in living systems. It represents an important step in the merging of disciplines to solve important problems at the interface of biology and engineering. Techniques that may be used to prepare membranes of the present invention include photolithography, diamond turning, diamond ruling and laser machining. Such techniques are well known to those of skill in the art, see e.g., Marc Madou, *Fundamentals of Microfabrication,* CRC Press, Baton Rouge, which describes casting processes at page 127 et seq., diamond tooling at page 351 et seq., and other techniques described in Table 7.7 therein at page 358–359. Those of skill in the art also are referred to *Polymer Processing and Structure Development* (Wilkinson and Ryan, Kluwer Academic Press), which describes various methods of polymer processing.

III. Modifying the Surface of the Micro-textured Membrane

Chemical bonding protocols which alter the surface chemistry of microtextured silicone and other substrata that form the membranes of the present invention will promote attachment, adhesion-dependent cell signaling and growth of cardiomyocytes in culture.

Neonatal rat cardiomyocytes readily attach to Type 1 collagen, laminin, and fibronectin-coated surfaces, but the noncovalent nature of the interaction between the ECM protein(s) and the supporting substrata are not ideal for the application of mechanical load. Upon large or repeated mechanical strains, cells detach from the commercially available silicone substrata. Here, the inventors have used chemical bonding techniques to covalently link adhesive peptides to the surface of flat and microtextured substrata as produced above. The effectiveness of these adhesive peptides in promoting cell attachment, growth and differentiation of the cardiomyocytes will be compared to flat and microtextured membranes coated with the parent ECM protein (i.e. fibronectin or laminin). The inventors propose to use the adhesive properties of two peptides derived from fibronectin and laminin, which will be covalently bonded to flat and microtextured elastic substrata. In addition, it should be noted that the microtextured membranes of the invention also may be formed using other integrins and adhesive peptides such as for example.

The techniques for covalently bonding peptides to a silicon surface can be performed by a variety of conventional methods using known coupling agents and known derivatization methods which are well known to those of skill in the art. This invention also relates to the covalent coupling of such peptides to the microtextured membrane surface either directly or via an appropriate linking or spacer group. U.S. Pat. No. 4,789,601, incorporated by reference in its entirety, describes a polyorganosiloxane composition having a biocompatible surface. The surface of the composition is treated with a primary amine or a peptide. This patent is incorporated herein by reference as teaching methods of modifying silicone surfaces.

U.S. Pat. No. 5,733,538, incorporated herein by reference, describes surface-modifying copolymers having cell adhesion properties. The surface modification techniques and polymers described therein also may be useful in conjunction with the present invention. More particularly, the patent discusses a hemocompatible surface-modifying additive for modifying polyurethane or polyurethane urea substrates. The additive has a polyurethane or polyurethane urea hard block or an alternative block which is miscible with the poly(urethane) or poly(urethane-urea) base polymer, a polysiloxane hydrophobic soft block, an optional hydrophilic spacer and a peptide selected from the group consisting of Arg-Gly-Asp, X-Arg-Gly-Asp (SEQ ID NO:4), Arg-Gly-Asp-X (SEQ ID NO:5) and X-Arg-Gly-Asp-X'(SEQ ID NO:6), wherein X and X' are amino acids.

In preferred aspects of the present invention, peptides or proteins are covalently bound to the silicone surface by the following multistep process. This process has been derived from, but altered in several ways, from that published previously (Ferguson et al., *Macromolecules* 26: 5870–5875, 1993. Xiao et al., *Langmuir,* 14: 5507–5516.)

A. A silicone membrane is chemically functionalized with OH groups by exposure to a 13.6 MHz, 20 W, continuous radio frequency discharge plasma of 0.8 mtorr of water for 4 minutes.

B. An amine group is attached to the silicone surface via reaction with a 5% (v/v) solution of 3-aminopropyltriethoxysilane (APTES) in ethanol for 1 hour at 60° C. under Ar atmosphere, then washed in ethanol.

C. A sulfo-maleimide cross-linker is attached to the amine group via reaction with a 0.2 mM solution of sulfo-SMCC (Pierce) prepared in a boric acid (0.2 M)/borax (0.05 M) buffer at pH of 7.5 for 30 minutes, then washed with the boric acid/borax buffer.

D. A cysteine-terminated peptide or protein is attached to the maleimide cross-linker by reaction with a 10–100 μM peptide solution in 0.1 M degassed phosphate buffer (pH 6.6) containing 1.2% (v/v) Tween 80 for 20 hours. The peptide functionalized silicone is then washed by exposure to 13.9 mM SDS for 20 hours at room temperature.

Step D was demonstrated using the 15-residue peptide, acetyl-CGGEGYGEGRGDSPG-amide (SEQ ID NO:3), but it can be performed using any cysteine-terminated peptide or protein. For example, the laminin derived peptide YIGSRC (SEQ ID NO:2) can also be bound in this fashion, via a peptide tether. Mixtures of the two peptides can be readily prepared from mixtures of their solutions. Polyethylene glycol can be bound along with the peptides or proteins to the silicone surface, to resist non-specific protein adsorption during cell growth. The entire process has been performed on both flat and microtextured silicone membranes. Those of skill in the art are referred to Lateef et al., which provides additional teachings of peptide-surface modification (Lateef et al., *Amer. Chem. Soc. Polym. Mater. Sci. Engin. Prepr.* 85:403–404, 2001).

Selective removal of the amine produced by Step A. can be achieved by low energy argon ion bombardment of the membranes (Ada, et al., *J. Vac. Sci. Technol.* B 13: 2189–2196, 1995). Alternatively, an Ar plasma treatment might also allow this amine removal. The selective removal of amine prior to Step B will ensure that peptide functionalization will only occur on the walls of the microtextured membranes.

Analysis of the Cardiomyocyte Adhesive and Growth-promoting Properties of the Microtextured "peg and groove" Silicone Membranes in which GRGDSP (fibronectin receptor ligand; SEQ ID NO:1) and the YIGSRC (laminin receptor ligand; SEQ ID NO:2) are Covalently Bound to their Surfaces.

Cell attachment efficiency can be analyzed as previously described (Samarel and Engelmann, *Am J Physiol* 261, H1067–77, 1991). Briefly, plating efficiency is analyzed as the amount of recovered DNA from adherent cells 4 h after plating compared to the amount of DNA in the plating suspension. In the case of Type I collagen-coated plastic dishes, plating efficiency of freshly isolated neonatal rat ventricular myocytes was 68±4% (Samarel and Engelmann, *Am J Physiol* 261, H1067–77, 1991). It is expected that plating efficiency will vary between flat and microtextured surfaces, and with the two peptides (whether used alone or in combination).

Adhesion-dependent Cell Signaling

Adhesion of cardiomyocytes to a flat, plastic substratum coated with Type I collagen increased the cellular content of tyrosine-phosphorylated proteins over time. Similar experiments can be conducted with flat and microtextured membranes containing covalently bound GRGDSP (SEQ ID NO:1) and YIGSRC (SEQ ID NO:2). In addition, adhesion-dependent activation of growth-related signaling cascades can be analyzed and the cellular content of tyrosine-phosphorylated FAK, paxillin and vinculin can be analyzed by immunoprecipitation with phosphotyrosine-specific antibody, and Western blotting with antibodies specific for the cytoskeletal proteins (Eble et al., *In The Hypertrophied Heart,* Takeda N, Dhalla NS, eds., Kluwer Academic Publishers, Boston, 1999). The degree of adhesion-dependent activation of downstream MAPK cascades also may be assessed using quantitative Western blotting. Antibodies specific to the phosphorylated forms of ERK1/2, iNK and p38 MAP kinases may be usefully employed in this endeavor. Activation of adhesion-dependent cell signaling will vary between flat and microtextured surfaces, and with the two peptides (whether used alone or in combination).

Cell Growth and Differentiation

In addition to these "acute" adhesion studies, the effects of the different microtextured, functionalized silicone membranes on specific growth parameters of the adherent cardiomyocytes can be examined. Total protein/DNA and α- and β-MyHC/DNA can be determined 48–72 h after initial plating using well-established techniques known in the art (Eble et al., *Am. J. Physiol.* 274: C1226–C1237, 1998). These measurements can be correlated with measurements of total cell volume and sarcomeric assembly obtained by confocal microscopy. MyHC synthetic rate may be measured by [$^3$H]leucine pulse-labeling, and MyHC protein half-life analyzed in [$^{35}$5]methionine pulse-chase biosynthetic labeling (Samarel et al., *Am J Physiol* 263, C642–52, 1992). Previous studies from the inventors laboratories indicate that sarcomeric assembly and cardiomyocyte hypertrophy are closely correlated with both enhanced MyHC synthesis and stability (Eble et al., *Am J Physiol.* 274:C1226–C1237, 1998). MyHC synthesis and turnover thus serve as useful surrogate markers of cardiomyocyte growth and differentiation. In other words, 3-D cardiomyocytes maintained on microtextured substrata with optimal concentrations of functionalized peptides should demonstrate higher rates of MyHC synthesis and accumulation than their 2-D counterparts. Finally, the cellular content of FAK, paxillin, vinculin and β1-integrins can be analyzed by quantitative Western blotting (Sharp et al., *Am J Physiol,* 42: H546–H556, 1997; Eble et al., *In The Hypertrophied Heart,* Takeda N, Dhalla NS, eds., Kluwer Academic Publishers, Boston, 1999), and correlated with confocal immunocytochemical studies of focal adhesion formation of cells grown on flat vs. microtextured substrata derivatized with the two integrin receptor ligands. The amounts of these focal adhesion and cytoskeletal proteins will vary between flat and microtextured surfaces, and with the two peptides (whether used alone or in combination).

Myocyte Morphology in Response to Different Plating Substrates

Recent studies have revealed the importance of ECM-cell interactions in myocyte attachment and spreading. In these studies, freshly isolated neonatal rat cardiac myocytes plated onto flat, plastic surfaces coated with various ECM components demonstrate different degrees of cell attachment and spreading depending on the type of ECM protein employed. Cells attach and spread to plastic surfaces coated with Type I collagen, Type IV collagen or fibronectin (Eble et al., *Am J Physiol Heart Circ Physiol.*, 278(5):H1695–H1707, 2000). However, laminin alone does not support cell attachment and spreading as well as the other ECM components tested, whereas poly-L-lysine provides a poor adhesive surface. These results are in keeping with the relative abundance of collagen-, fibronectin- and laminin-specific β1-integrins on the cell surface of neonatal cardiomyocytes (Terracio et al., *Circ. Res.* 68:734–744, 1991).

Neonatal rat ventricular myocytes may be isolated and plated overnight at high density onto plastic dishes pre-coated with either collagen I (Col I), collagen IV (Col IV), fibronectin (FBN), laminin (LMN), or poly-L-lysine (Poly (Lys)). The myocytes are then maintained in serum-free culture medium for 48 hours. Hoffman modulation contrast micrographs show that plates pre-coated with Col I, Col IV and FBN seem to be the best substrates for myocyte attachment and spreading. Myocytes plated on the LMN and Poly(Lys) pre-coated dishes attached less well and appeared less well spread.

Adhesion-dependent Increases in Phosphotyrosinylated Proteins in Control and Verapamil-treated Myocytes The interaction of cardiac myocytes with an ECM substratum not only provides a physical site for cell attachment and spreading, but also initiates a series of cell signaling events leading to structural reorganization and growth of the cardiac muscle cell. Protein tyrosine phosphorylation is one type of cell signaling event that occurs in response to integrin engagement and cell adhesion. A similar degree of protein tyrosine phosphorylation occurs in response to neurohormonal stimulation of the angiotensin II or endothelin receptor on the myocyte cell surface. Cell attachment and spreading on a flat, collagen-coated substratum induces the tyrosine phosphorylation of a variety of intracellular proteins (Eble et al., *Am J Physiol Heart Circ Physiol.*, 278(5): H1695–H1707, 2000). Many of these tyrosine-phosphorylated proteins are localized in focal adhesions (Strait et al., *Am J Physiol Heart Circ Physiol.*, 280(2): H756–H766, 2001). However, tyrosine phosphorylation of cytoskeletal and other myocyte proteins is markedly reduced in cells maintained in plating medium containing the L-type Ca channel blocker verapamil, a potent inhibitor of focal adhesion and costamere formation in cardiomyocytes (Sharp et al., *Am. J. Physiol,* 42: H546–H556, 1997). This provides another method with which to monitor the effects of cell attachment, spreading, and signaling on flat vs. microtextured substrata that are chemically modified with different adhesive peptides.

Localization of Myosin Heavy Chain, Paxillin, Tyrosine-phosphorylated Proteins, and Focal Adhesion Kinase in Neonatal Rat Ventricular Myocytes Adhesion and growth of myocytes maintained on chemically modified, microtextured silicone and other substrata can also be monitored by confocal immunolocalization of specific sarcomeric and cytoskeletal proteins (Deutsch et al., *J Biomed Mater Res. Applied Biomaterials*, 53: 267–275, 2000). Cardiac myocytes plated onto plastic substratum coated with Type I collagen or laminin, display a typical "fried egg" appearance, with few, poorly organized sarcomeres as revealed here by staining with a monoclonal antibody specific for sarcomeric MyHC. Focal adhesions, can be visualized with a monoclonal antibody specific for the cytoskeletal protein paxillin and are found predominantly at the bottom of the cell, and along the membrane periphery. Focal adhesions are also the predominant sites for the localization of phosphotyrosinylated proteins, which include paxillin, vinculin and the nonreceptor protein tyrosine kinase FAK. Similar immunocytochemical techniques can be used to monitor the distribution and amounts of focal adhesion proteins on microtextured as compared to flat substrata which have been chemically modified with integrin-binding peptides.

To monitor localization of contractile and signaling proteins in neonatal rat ventricular myocytes, cells may be cultured in serum-free medium alone for 48 h, then fixed, permeabilized, and stained using antibodies specific for sarcomeric MyHC; the cytoskeletal protein paxillin; proteins containing phosphorylated tyrosines; and FAK.

Using the above outlined studies, those of skill in the art should be able to produce membranes that will promote myocyte adhesion and orientation, as well as produce cells with numerous focal adhesions and costameres that are necessary for sarcomere assembly. The selection of the optimal membrane microtopography can be based upon carefully defined criteria which critically evaluate shape, structure and function of the cells. The development of optically clear, microtextured membranes with covalently bonded adhesive peptides should provide the necessary substratum with which to apply static or cyclic mechanical load without the problems of cell detachment.

IV. Establishing a Myocyte Cell Culture

The present invention can be employed in the in vitro growth of any of a variety of cells including but not limited to myocardial cells, bone cells, connective tissues, endothelial cells, smooth and skeletal muscle. The cells may be primary cells or may be cell lines derived from such primary cells, tumors and the like. Cell lines derived from muscle may be obtained from a cell line depository such as for example American Type Culture Collection (ATCC, Bethesda, Md.). Such cell lines may be smooth muscle cell line, cardiac cell lines, skeletal muscle cells lines and the like. Further, the cell lines may be fibroblast cell lines that are capable of differentiating into myocardial cells. The conditions for growth of the specific cell line purchased will depend on the biological source and generally instructions for the growth of the cells are made available along with the cell lines from ATCC.

Preferably, the cell lines are able to differentiate into cells that possess contractile function. Specifically preferred cells are embryonic or adult stem cells. The cells may be derived from any vertebrate or non-vertebrate animal source. For example, the animal source may be human, monkey or other primate, mouse, rat, rabbit, cat, dog, goat, sheep, pig, horse, cow, fish, bird or any other animal from which such cells may be harvested. Preferably, the cells for the culture in the present invention are mammalian cells. More preferably, the cells are human or primate cells, but rat and mouse cells also will be usefully employed herein. Examples of cell lines and their culture on the platforms of the present invention are detailed in the examples section. The cells are inoculated onto the substrata. The appropriate growth factors, may be added to the culture prior to, during or subsequent to inoculation of the myocyte cells. The concentration of such factors maintained in the cultures can be monitored and adjusted to optimize growth.

Where the cells used are primary cells, they may be readily isolated by disaggregating an appropriate organ or tissue which is to serve as the source of the cells being grown. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, *Culture of Animal Cells. A Manual of Basic Technique,* 2d Ed., A. R. Liss, Inc., New York, 1987, Ch. 9, pp. 107–126.

Once the tissue has been reduced to a suspension of individual cells, the suspension can be fractionated into subpopulations from which the myocyte and/or fibroblast cells can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, *Culture of Animal Cells. A Manual of Basic Techniques,* 2d Ed., A. R. Liss, Inc., New York, 1987, Ch. 11 and 12, pp. 137–168.

In specific examples, the isolation of myocytes may, for example, be carried out as follows: fresh muscle tissue is thoroughly washed and minced in an appropriate buffer in order to remove serum. The minced tissue is incubated from 1–12 hours in a freshly prepared solution of a dissociating enzyme such as trypsin, collagenase or the like. The cells are preplated onto uncoated plastic dishes to reduce non-muscle cell contamination. The cells are plated at a relatively high density of, for example, 1000–3000 cells/mm$^2$. Myocytes attach and spread overnight and may be maintained in serum medium.

It is possible that the cells cultured in this manner may be used for transplantation or implantation in vivo. In such cases, it is preferable to obtain the muscle cells from the patient's own tissues. After inoculation of the cells, the three-dimensional matrix should be incubated in an appropriate nutrient medium. Many commercially available media such as DMEM, RPMI 1640. Fisher's Iscove's, McCoy's, and the like may be suitable for use. It is important that the three-dimensional membrane be suspended or floated in the medium during the incubation period in order to maximize proliferative activity. In addition, the culture should be "fed" periodically to remove the spent media, depopulate released cells, and add fresh media.

These procedures are greatly facilitated when carried out using a bioreactor, which is a closed system housing the three-dimensional framework inoculated with muscle cells. A bioreactor reduces the possibility of contamination, maintains the cultures under intermittent and periodic pressurization to create environmental conditions that maintain an adequate supply of nutrients to myocyte cells throughout the cartilage tissue construct by convection.

During the incubation period, the muscle cells will grow linearly along and envelop and colonize the three-dimensional membrane before beginning to grow into the openings of the matrix. It is preferable to grow the cells to an appropriate degree which reflects the amount of myocyte cells present in the in vivo tissue.

V. Uses of the Three-Dimensional Culture System

The three-dimensional culture system of the invention can be used in a variety of applications. These include, but are not limited to, transplantation or implantation of either the cultured cells obtained from the matrix, or the cultured matrix itself in vivo; screening the effectiveness and cytotoxicity of compounds, allergens, growth/regulatory factors, pharmaceutical compounds, etc., in vitro; elucidating the mechanism of myocardial organogenesis; studying the mechanism by which drugs and/or growth factors operate, to name but a few.

The growth of fully functional cells on the membranes of the present invention is a step in the path towards myocardial organogenesis and cardiac and other muscle tissue engineering. Three-dimensional tissue culture implants may, according to the inventions, be used to replace or augment existing tissue, to introduce new or altered tissue, or to join together biological tissues or structures.

The three-dimensional cultures may be used in vitro to screen a wide variety of compounds, for effectiveness and cytotoxicity of pharmaceutical agents, growth/regulatory factors, anti-hypertensive agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed.

The three-dimensional cultures of the invention may be used as model systems for the study of physiologic or pathologic conditions. For example, the new culture system may be used to determine the limits of cell growth and mechanical signal transduction. Cardiac (high density, aligned, physiologically functional, micro-anatomically correct) myocytes grown on microtextured peg and groove membranes are maintained in the unstretched state (control). Cells will then be mechanically stimulated on the various microtextured and chemically bonded surfaces that have been generated by the present invention. In this manner, new chemically modified, micro-textured surfaces will produce addition of new myofibrils reproducing the hypertrophy observed in response to both physiological and pathological stimuli. These experiments will help provide a better understanding of the mechanisms involved in pathogenesis of heart failure and normal adaption to exercise.

Those of skill in the art will understand that cultures grown on the membranes of the present invention may have use as artificial organ/tissue patch applications such as those described in, for example, a variety of U.S. Patents which are incorporated herein by reference. For example, U.S. Pat.

No. 5,885,829 describes methods for regenerating dental and oral tissues from viable cells using ex vivo culture on a structural matrix. The regenerated oral tissues and tissue-matrix preparations thus provided have both clinical applications in dentistry and oral medicine. It is contemplated that the membranes and cell cultures of the present invention could similarly be employed to regenerate not only oral tissues but muscular, vascular and other tissue.

U.S. Pat. No. 5,721,131, incorporated herein by reference, describes a process for forming spatially oriented neo-vascular capillaries. It is contemplated that the membranes of the present invention could be used in combination with the ultra-thin film pattern of cell adhesion promoter and cell adhesion inhibitor wherein the cell adhesion promoters have a line-width of between about 50–490 µm. Such compositions could be seeded on the present membranes and be used to allow allowing the endothelial cells to differentiate into spatially oriented neo-vascular capillaries.

U.S. Pat. No. 5,855,610 describes improved yields of engineered tissue following implantation, and engineered tissue having enhanced mechanical strength and flexibility or pliability, can be obtained by implantation, preferably subcutaneously, of a fibrous polymeric matrix for a period of time sufficient to obtain ingrowth of fibrous tissue and/or blood vessels, which is then removed for subsequent implantation at the site where the implant is desired. The matrix is optionally seeded prior to the first implantation, after ingrowth of the fibrous tissue, or at the time of reimplantation. The method is particularly useful in making valves and tubular structures, especially heart valves and blood vessels. It may be that the membranes of the present invention also may find use in such a method for engineering tissue. As such, U.S. Pat. No. 5,855,610 is incorporated by reference as teaching such techniques.

U.S. Pat. No. 5,804,178, incorporated herein by reference, describes a method of implanting a matrix structure having cells attached thereto by providing a biocompatible polymeric matrix structure having attached thereto viable animal cells exhibiting normal growth and proliferation selected from the group consisting of endocrine cells, fibroblasts, endothelial cells, and genitourinary cells, which are allowed to attach thereto; and implanting the matrix structure having cells attached thereto into a patient in need thereof, wherein the matrix structure is juxtaposed with tissue having high surface area and vasculature; adjacent the surface of the tissue selected from the group consisting of mesentery, omentum and peritoneum, and wherein the matrix structure is configured to allow adequate nutrients and gas exchange between the attached cells and the blood for the cells to remain viable and to form tissue. The membranes of the present invention may similarly be used to produce an implantable patch of cells for purposes of tissue healing and/or regeneration.

In another example, U.S. Pat. No. 5,800,811, incorporated herein by reference, describes an artificial skin prepared by impregnating a collagen matrix with a transforming growth factor-β having a collagen-binding site to bind the growth factor to the collagen matrix, incubating the impregnated matrix with a source of fibroblasts and mesenchymal stem cells to form a captured population of mesenchymal stem cells within the impregnated matrix and incubating the resultant matrix with a source of keratinocytes which epithelialize the matrix to form an artificial skin. The membranes of the present invention could serve as a useful matrix in such techniques for generating artificial skin and as such would be extremely useful in for example treating burns or other skin tissue injuries.

Grafting cells into organs such as the brain also are contemplated. Such techniques are described in e.g., U.S. Pat. No. 5,750,103 in which a cellular graft is introduced into the brain of a mammalian subject by attaching the cells to a support matrix so that the cell attaches to the matrix surface, and implanting the support matrix with the attached cell into the brain. A membrane of the invention could act as such an implantable support.

VI. EXAMPLES

The following examples present preferred embodiments and techniques, but are not intended to be limiting. Those of skill in the art will, in light of the present disclosure, appreciate that many changes can be made in the specific materials and methods which are disclosed and still obtain a like or similar result without departing from the spirit and scope of the invention.

Example 1

Materials and Methods

The present example provides details of materials and methods employed throughout the application and in the Examples presented herein below.

Polymeric Microtextured Membrane Preparation

Control silicone membranes are prepared using silicone membranes (Specialty Manufacture, MI) that are pre-treated with ION HCl for 2 hours before coating with laminin to allow the cells to adhere. The microtextured polymeric membranes will be fabricated by a technique where photolithographically defined silicon wafers are used as templates or molds for reproducing complimentary images on desired polymers. This enables the reproduction of precise surface architectures and geometries.

Silicone microtextured surfaces are produced using a method developed in the Desai laboratory as described herein throughout. Starting with a clean silicon wafer, approximately 1 ml of UV light sensitive negatice photoresist is spun on the wafer for 30 seconds at 1500 rpm. This results in PR thickness of approximately 10 microns. The photoresist is soft baked for 6 minutes at 95° C. The wafer is lithographically patterned with arrays of 10 by 10 by 10 µm (L×W×H) pegs by exposure to 20 mW UV light for 10 seconds. It is then hard baked for 4 minutes at 95° C. and then the pattern is developed. A parylene layer is deposited on the patterned photoresist and then peeled off, resulting in a parylene microtextured mold. Silicone gel (or any other polymeric system) is prepared by mixing elastomer and catalyst in a 10:1 ratio and gently spreading over the parylene mold. After polymer curing (~48 h) the microtextured membranes are subsequently coated with a thin layer of laminin, or other bio-acceptable moiety.

Neonatal Rat Primary Cardiac Culture

Myocytes are isolated from the cardiac ventricles of 1–2-day old Sprague-Dawley rats by sequential collagenase digestion, as previously described (Samarel and Engelmann, *Am J Physiol* 261, H1067–77, 1991). Cells are pre-plated onto uncoated plastic dishes (60 mm) to reduce non-muscle cell contamination, and cells are plated at high density (1000–2000 cells/mm$^2$) onto the various substrata (Goldspink et al., *Am J. Physiol.* 271: H2584–H2590, 1996). Myocytes attach and spread overnight, and are then maintained in serum-medium for 48 h. Cells are grown on various silicone membranes at high density. All chemical and culture materials, unless otherwise specified, are obtained from Sigma Chemical, St. Louis, Mo.

The Degree of Orientation

The images are selected at random. Orientation is measured stereologically using digital images of the cells taken using e.g., an ImagePoint 1.3. Images are overlaid by a neon green parallel lined grid. A count is taken of the number of intersections between the 0° lines and myofibrils. Another count is also made of intersections between the 90° lines and myofibrils. To compute % orientation the following formula is used:

% orientation=$(I\alpha-i/(\alpha+I))\times 100$, where $\alpha=90°$ intersections and $I=0°$ intersections Image Analysis Samples for each experiment are coded to remove subjective bias. At high magnification light microscopy, selection of alternate fields yields at least 30 cells per experiment. Five separate tissue culture experiments are analyzed for each condition. Images of cells closest to the center of the alternating fields across the coverslip are captured digitally in the Russell lab using a peltier cooled CCD video camera (Photometrics Image Point camera, Photometrics Ltd, Tucson, Ariz.). Image processing and analysis is performed using the Image-Pro Plus system software version 3.0.01 for 95/NT (Media Cybernetics, Silver Spring, Md.) or similar software. The intensity (grey scale values) along a calibrated line for each cell is measured.

Confocal Measures

The Zeiss LSM 510 confocal microscope has computer graphics that enable the cell to be treated in 3D space at 0.1 $\mu$m intervals. Cells are selected in a systematic random manner to provide statistically valid samples from at least five different cell cultures (Perhonen et al., *J Mol Cell Cardiol.*30: 1713–1722, 1998). Total myocyte cell and myofibril heights are assessed by scanning from the bottom to the top of the cell at three locations: (1) the center of the nucleus, (2) 15 $\mu$m from the edge of the nucleus where cells grown on flat membranes are 30% of their maximum height (Goldspink et al., *J Cell Sci* 110: 2969–2978, 1997), and (3) near the peg for pegged membranes. The frequency of peg attachment by a myocyte is measured with phase microscopy or conventional epi-fluorescence. Attachment is measured as the binding of a cell to an actual peg compared to a virtual one (flat membrane with pseudo-pegs superimposed over the image). This is an important distinction as it corrects for random occurrences. All the cells within a 160×240 $\mu$m$^2$ area are used to analyze attachment to the peg.

Immuno-chemistry of Contractile, Focal Adhesion and Costameric Proteins

Cells are fixed (15 min, room temperature) with 2% (w/v) paraformaldehyde in PBS, washed (15 min) in 1% (w/v) glycine in PBS, and permeabilized (15 mm) with 0.5% (v/v) Triton X-100 in PBS. Myocytes are then stained with commercially available antibodies to Myl-IC, paxillin, phosphotyrosine, vinculin, $\beta$1 integrin, and FAK. Appropriate FITC or rhodamine conjugated secondary antibodies are used to visualize the specific proteins. Fluorescently labeled cells are then viewed using a Zeiss Model LSM 410 or 510 laser scanning confocal microscope. Multiple optical sections approximately 1 $\mu$M thick are taken of each sample to eliminate out-of-focus fluorescence of the intensely stained myocytes.

Biochemical Composition of Cultured Neonatal Rat Ventricular Myocytes

For the quantitative analysis of total cellular protein and DNA content, cells are washed twice in HBSS, and 0.2N perchloric acid (1 ml) is added. The precipitated macromolecules are then quantitatively scraped from the dishes and collected by centrifugation (10,000 g, 10 min). The precipitate is redissolved by incubation (60° C., 20 min) in 250 $\mu$l of 0.3N KOH. Aliquots are then used for analysis of total protein by the Lowry method using crystalline human serum albumin as standard, and for DNA using 33258 Hoecht dye and salmon sperm DNA as standard, as previously described (Samarel and Engelmann, *Am J Physiol* 261, H1067–77, 1991). For quantitative analysis of $\alpha$-MyHC and $\beta$-MyHC content, cells are washed twice in HBSS and lysed in 250 ml of sample buffer [62.5 mM Tris-HCl, pH 6.8, containing 8% (w/v) of sodium dodecyl sulphate (SDS), 5% (v/v) 2-mercaptoethanol, and 10% (w/v) glycerol]. The concentrations of $\alpha$-MyHC and $\beta$-MyHC isoenzymes are assessed by SDS-polyacrylamide gel electrophoresis and silver staining (Samarel and Engelmann, *Am J Physiol* 261, H1067–77, 1991). MyHC band intensity is quantified by laser densitometry, and compared to the band intensity of purified MyHC standards (0–300 ng). The positions of the $\alpha$-MyHC and $\beta$-MyHC bands are confirmed by electrophoresis of $\alpha$-MyHC and $\beta$-MyHC protein standards obtained from normal and hypothyroid adult rat hearts, respectively; and by Western blotting with an anti-MyHC antibody that cross reacts equally with both isoenzymes.

Immuno Precipitation and Western Blotting for Analysis of Adhesion-dependent Cell Signaling Neonatal rat ventricular myocytes are rinsed with cold PBS and then scraped in ice-cold lysis buffer according to Schlaepfer and Hunter (Schlaepfer and Hunter, 1996) 150 mM Hepes, pH 7.4 containing 150 mM sodium chloride, 10% glycerol, 1.5 mM magnesium chloride, 1 mM EGTA, 1 mM sodium vanadate, 10 mM sodium pyrophosphate, 100 mM sodium fluoride, 1% Triton X-100, 0.1% SDS, 1% sodium deoxycholate, 10 $\mu$g/ml leupeptin, 10 mg/ml aprotinin and 1 mM Pefabloc (AEBSF)]. Protein concentrations are assessed using a bicinchoninic acid assay (Pierce, Rockford, Ill.) and then equal amounts of protein are immunoprecipitated with anti-FAK, paxillin, vinculin, or phosphotyrosine antibodies. Immune complexes are collected by incubation with Protein A plus protein G agarose beads or protein A or G beads alone for 2 hours at 4° C. The beads are centrifuged, washed in Triton-only lysis buffer (lysis buffer without sodium deoxycholate and SDS), and then in a Hepes buffer containing only sodium chloride, Triton X-100, and glycerol. The beads are then resuspended in 8% SDS sample buffer and boiled to release the proteins. Proteins are separated by 7.5% SDS-PAGE and transferred to nitrocellulose membranes (Hybond, Amersham, Arlington Heights, Ill.). Blots containing anti-phosphotyrosine immunoprecipitates are probed with anti-FAK, vinculin or anti-paxillin antibodies. The blots containing FAK, vinculin, or paxillin immunoprecipitates are probed with an anti-phosphotyrosine antibody. Horseradish peroxidase-conjugated goat anti-mouse or goat anti-rabbit secondary antibodies are visualized by enhanced chemiluminescence (ECL, Amersham, Arlington Heights, Ill.). The bands corresponding to FAK, or paxillin were quantified by laser densitometry.

Application of Extrinsic Mechanical Load

Cyclic mechanical deformation is produced with a Flexercell Strain Unit (Model FX-3000, Flexercell International, McKeesport. Pa.), at varying cycles per mm and maximal strain for up to 48–72 h (Cadre et al., *J. Mol. Cell. Cardiol.* 30;2247–2259, 1998). In brief, the Flexercell Strain Unit consists of a vacuum manifold regulated by solenoid valves that is controlled by a personal computer. The bottoms of the culture dishes are inserted into an airtight, sealed diaphragm atop the vacuum manifold and the entire apparatus is placed inside a humidified $CO_2$ incubator. When vacuum is applied to the bottoms of the culture plates, the membrane bottoms are stretched to a user-defined percentage of elongation (% strain). Varying patterns of strain (e.g. sinusoidal, stepwise, sustained, etc.) can be readily programmed using factory-installed protocols.

MAPK Activation

Different methods may be used to assess ERK1/ERK2 activation in cardiomyocytes, the mobility shift Western blot, the "in-the-gel-kinase" (ITKA) assay, and quantitative Western blotting of cell extracts using a phosphospecific ERK1/ERK2 antibody (Promega). Methodological details of the mobility shift and 1TKA are found in Sabri et al., (1998a). An immune complex assay with myelin basic protein as substrate also may be used, if necessary, to provide better quantitative results. JNK and p38MAPK activation are assessed by quantitative Western blotting with phospho-specific MAPK antibodies (Promega and New England Biolabs, respectively).

[$^3$H]leucine Biosynthetic Labeling

Pulse biosynthetic labeling experiments are performed to assess MyHC fractional synthetic rates as previously described (Samarel et al., *Am J Physiol* 263, C642–52, 1992; Sharp et al., *Circ.Res.* 73: 172–183,1993). MyHC fractional synthetic rates (Ks, %/h) are estimated from the following formula:

$$Ks=100[P^*/(F^* \cdot t)]$$

where P* and F* are the leucine specific radioactivities in MyHC protein and medium, respectively, and t is the labeling time in hours. Pulse-chase biosynthetic labeling. MyHC degradation is assessed in pulse-chase biosynthetic labeling experiments, as previously described (Samarel et al., *Am J Physiol* 263, C642–52, 1992; Sharp et al, *Circ.Res.* 73: 172–183, 1993; Eble et al., *Am. J. Physiol.* 274:C1226–C1237, 1998). Cells are incubated (24 h, 37° C.) in myocyte growth medium supplemented with 8 µCi/ml of [$^{35}$S]methionine. At the end of the pulse-labeling period, cells are rapidly rinsed twice in HBSS and either harvested by addition of 500 ml of SDS sample buffer, or chased for 24 h in growth medium supplemented with 2 mM unlabeled methionine. Cell samples are then separated by SDS-PAGE on 180 mm long, 0.7 mm thick, 7–17% vertical gradient SDS-PAGE gel. In each experiment, a constant fraction of the total protein of each culture dish is applied to individual gel lanes. This ensures that for all pulse-chase experiments, the amount of radioactivity in MyHC declines by decay rather than by simple dilution. After electrophoresis, gels are autoradiographed with fluorographic enhancement. Dried gels are exposed to unflashed Kodak XAR-5 film for varying time periods (24 days) at –80° C. Individual MyHC bands on the autoradiographs are scanned three times, and the average area beneath the MyHC peak is computed by autointegration. Linearity of detection of radioactivity by fluorography is assessed as previously described (Samarel et al., *Am J Physiol* 263, C642–52, 1992). The fractional rate of MyHC degradation (MyHC Kd, % Ihour) for each condition is estimated by the following formula:

$$MyHC\ Kd=100[\ln(MyHC\ AU)_0-\ln(MyHC\ AU)_{24}]/24$$

where $\ln(MyHC\ AU)_0$ and $\ln(MyHC\ AU)_{24}$ are the natural logarithms of the average absorbance (in arbitrary absorbance units) of the MyHC bands at times 0 and 24 hours of the chase. MyHC Kd values are then converted to apparent half-lives (in hours) according to the following formula:

$$MyHCt_{1/2} =100[in(MyHC\ AU)_0-\ln(MyHC\ AU)_{24}]/24$$

Example 2

Use of Surface Microtopography to Determine Cell Attachment and Shape

Microtextured membranes are created using photolithography and microfabrication techniques described herein above. FIG. 1 shows micro-pegged silicone membrane of the present invention viewed with phase microscopy. This membrane has rows of micro-pegs, each 10 µm high spaced 30 µm center to center along the row with 100 µm between the rows (center to center).

Figure 2A:
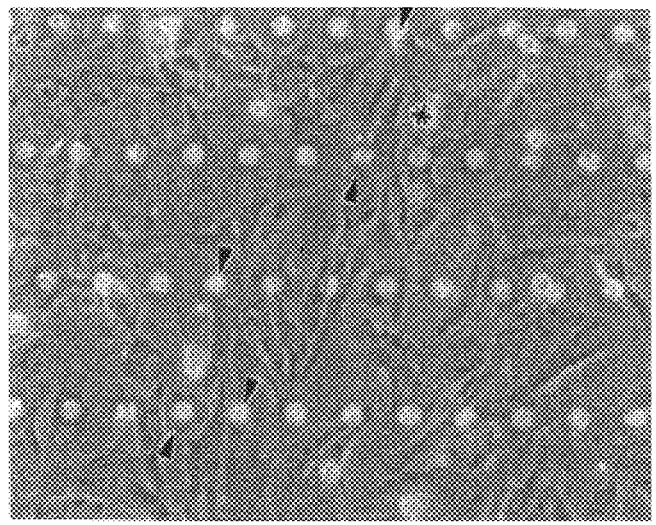
FIG. 2A shows cardiac myocyte cultures growing on a "pegged" silicone membrane coated with laminin.
Figure 2B:
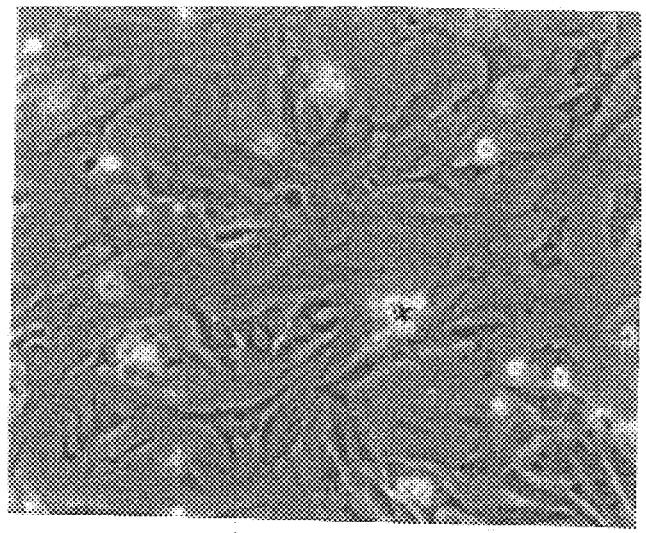
FIG. 2B shows cells grown on a silicone membrane without pegs.
Figure 3A:
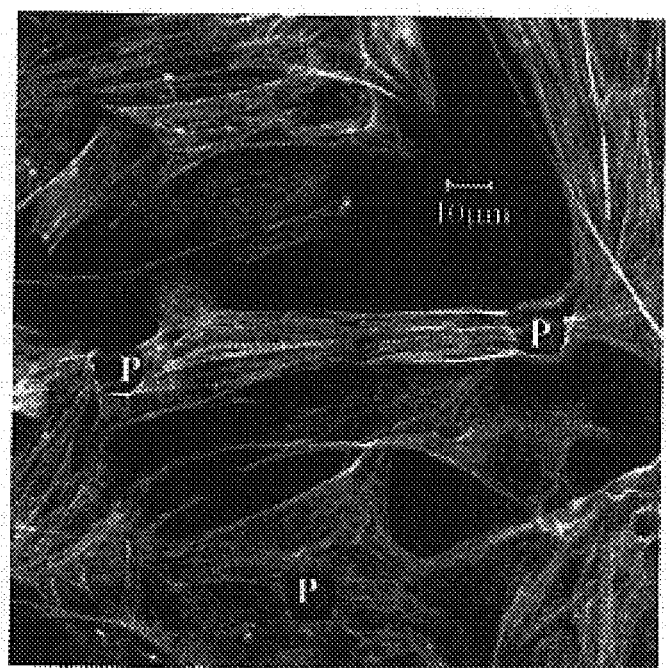
FIG. 3A: two myocytes end-to-end span the gap between two pegs.
Figure 3B:
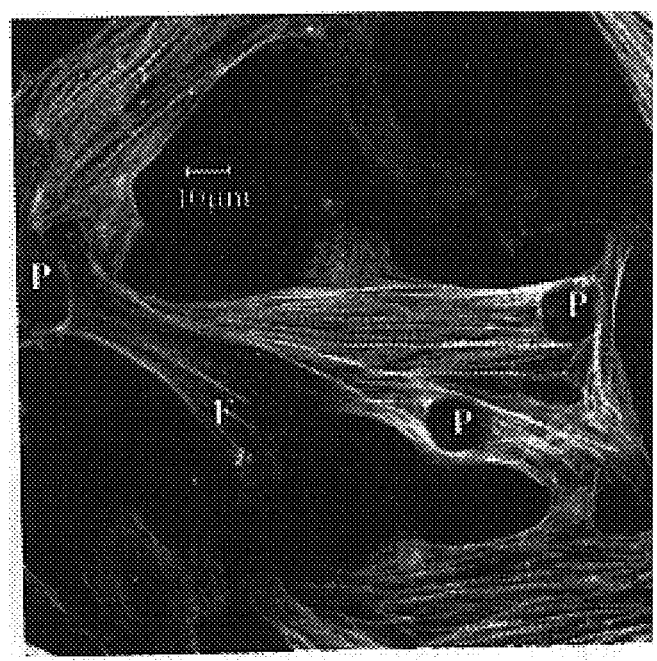
FIG. 3B: Another myocyte seen attaching to a 10 µm diameter micro-peg at one end and to a fibroblast (F) at the other end.
Figure 4:
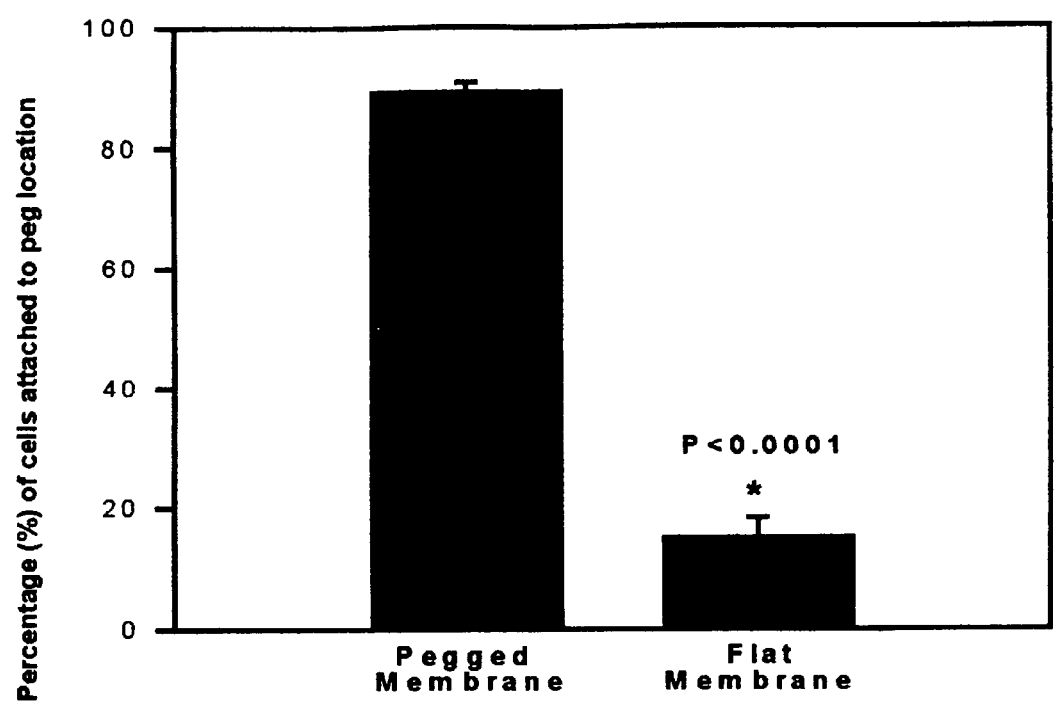
FIG. 4 shows a histogram of degree of cell attachment in which attachment is measured as the binding of a cell to an actual peg compared to a virtual one (flat membrane with pseudo-pegs superimposed over the image).

Primary rat neonatal cardiac myocytes were plated on laminin coated flat silicone membranes or those with micro-pegs 10 µm high to allow for perpendicular attachment. The changes in morphology were assessed by comparing the frequency of peg attachment and cell height and this reveals excellent myocyte shape and peg adhesion. FIG. 2A shows cardiac myocyte cultures growing on a "pegged" silicone membrane coated with laminin. This membrane has rows of micro-pegs, each 10 µm high (seen as rows of bright circles) spaced 30 µm center to center along the row and 100 µm between the rows, center to center. Note that the cardiac myocytes frequently terminate with a blunt end on a peg (arrows). There is also a tendency for the cells to straddle between the rows giving an oriented appearance. FIG. 2B shows cells grown on a silicone membrane without pegs. These traditionally grown myocytes are randomly oriented and have tapered rather than blunt ends. The randomly dispersed circular blobs (asterisk) are tissue debris. FIG. 3 shows cardiac attachment to micro-pegs (P) and intercalated disc. Horizontal views are seen with confocal microscopy where myofibrils are light in this culture (actin seen by phalloidin staining). FIG. 3A: two myocytes end-to-end span the gap between two pegs. The cells are connected by an intercalated disc, rarely seen in conventional tissue culture. FIG. 3B: Another myocyte seen attaching to a 10 µm diameter micro-peg at one end and to a fibroblast (F) at the other end. Note that the myocyte ends with a circular attachment to a peg (P) and the striated myofibrils (light, actin seen with phalloidin stain) lie in parallel bundles throughout the cell. FIG. 4 shows a histogram of degree of cell attachment in which attachment is measured as the binding of a cell to an actual peg compared to a virtual one (flat membrane with pseudo-pegs superimposed over the image). All the cells within a 160×240 µm$^2$ area from 3 different cultures were used to analyze attachment to the peg. Cells plated on pegged membranes attach more often (89.6±1.2%; n=3) to an actual peg than cells attaching to a virtual peg (15.4±3.0%; P<0.0001).

Figure 5:
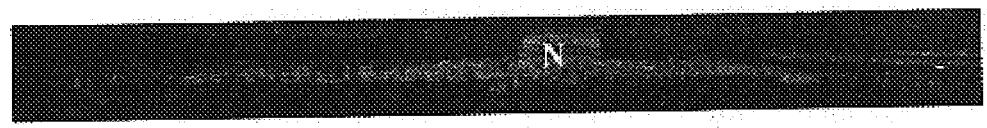
FIG. 5 shows a vertical view to show narrow myofibril layer in a cardiac myocyte grown on conventional flat membrane.
Figure 6A:
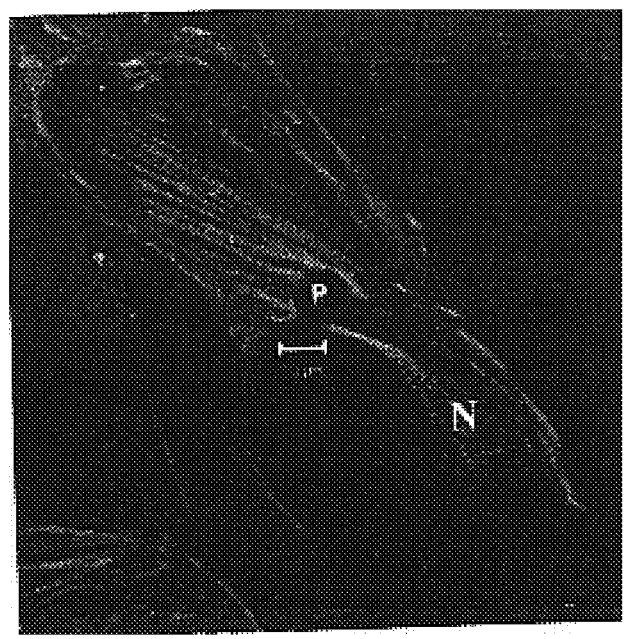
In FIG. 6A: the cells are seen with confocal microscopy, as above.
Figure 6B:
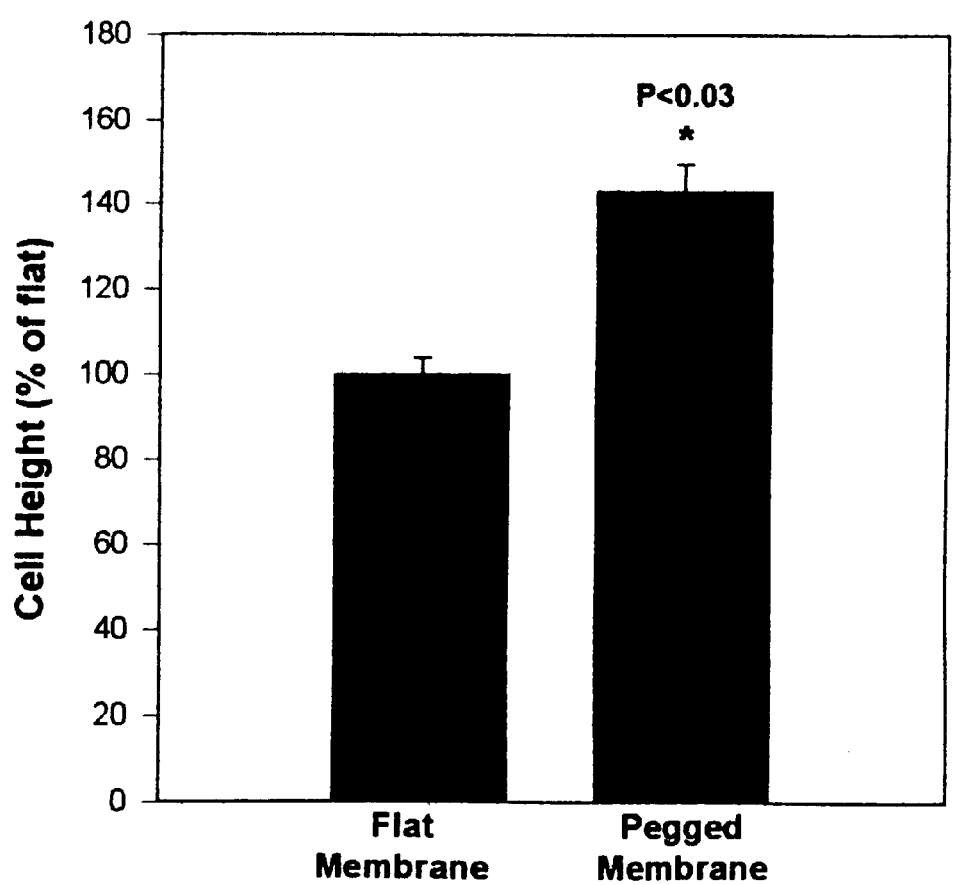
FIG. 6B shows a histogram to show increased cell height of cell grown on pegged membranes.

Myofibrils only form on the bottom surface of muscle cells in culture using electron microscopy (Eisenberg, *Am. J. Physiol.* 22;C349–C363, 1987). This myofibril layer can now be rapidly viewed with image analysis of confocal serial sections below by rotating the Z-stack into the Z-Y plane. FIG. 5 shows a vertical view to show narrow myofibril layer in a cardiac myocyte grown on conventional flat membrane. Note below that the striated myofibrils (red, phalloidin stain) lie in parallel bundles close to the bottom of the cell and below the nucleus, N, (purple, DAPI stain), giving the abnormal appearance of a "fried egg." FIG. 6 shows cell nucleus and myofibrillar architecture at micro-pegs (P), and cell height. In FIG. 6A: the cells are seen with confocal microscopy, as above. Note that the myofibrils reach to the end of the cell instead of the tapering into stress cables seen in traditionally cultured cells. In 3D rotation of this image the myofibrils enclose the nucleus. The cell has the a more life-like cylindrical shape. FIG. 6B shows a histogram to show increased cell height of cell grown on pegged membranes. Confocal microscopy was used to measure the total height of the cell. Cells plated on pegged membranes are 42.9±2.1% (n=2) higher than cells grown on flat membranes (P=0.03).

The inventors conclude that the 3D topography of the surface affects cardiac myocyte architecture and that cells prefer to terminate on a vertical structure with a subsequent increase in cell height.

Example 3

Altering the Surface Chemistry of the Microtextured Membranes

This Example deals with chemical bonding protocols which alter the surface chemistry of microtextured silicone and other substrata to promote attachment, adhesion-dependent cell signaling and growth of cardiomyocytes in culture.

Figure 7A:
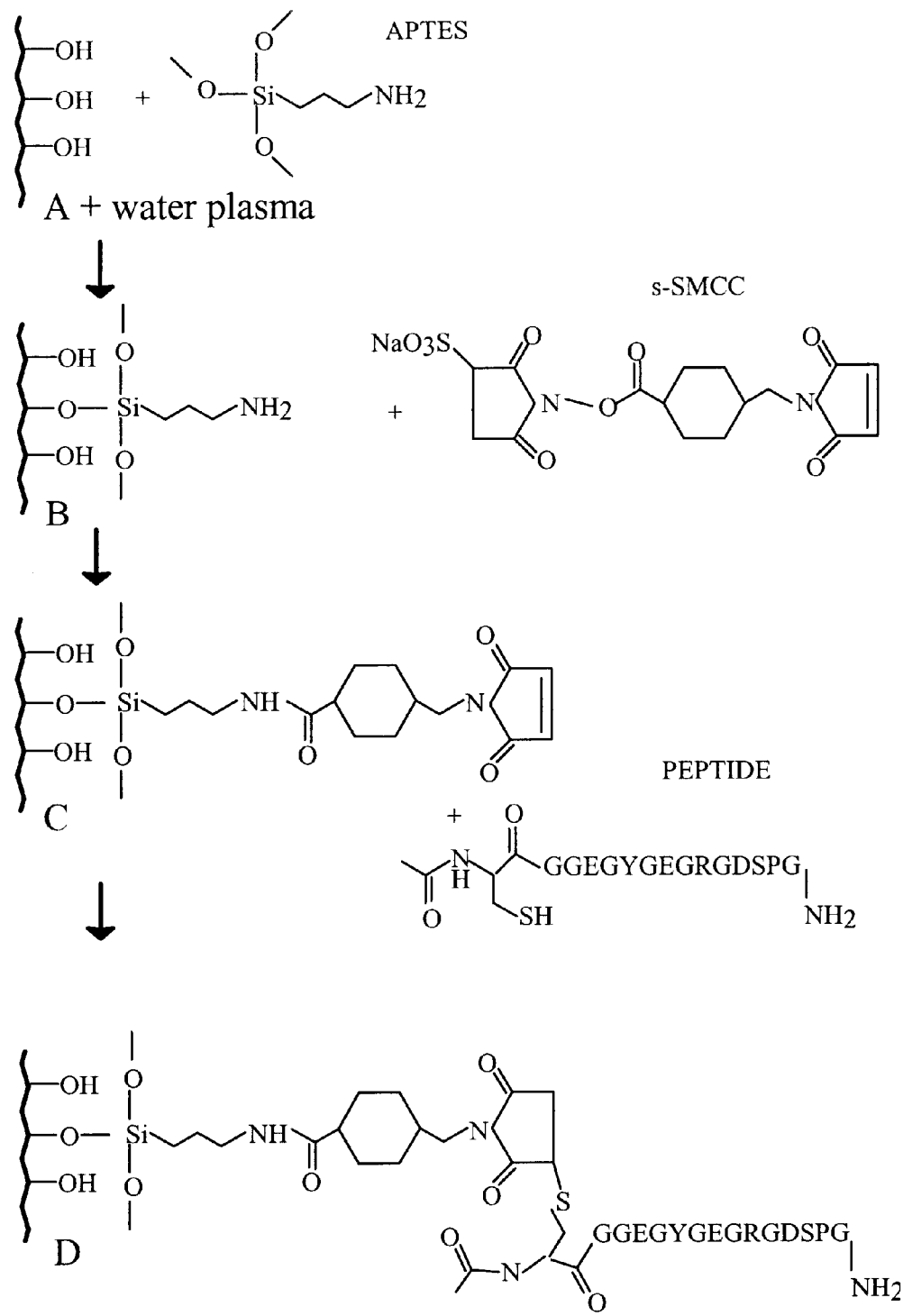
FIG. 7A shows the reaction steps in the surface chemical modification of silicone membranes: blank silicone (top), APTES, maleimide and peptide (bottom).
Figure 7B:
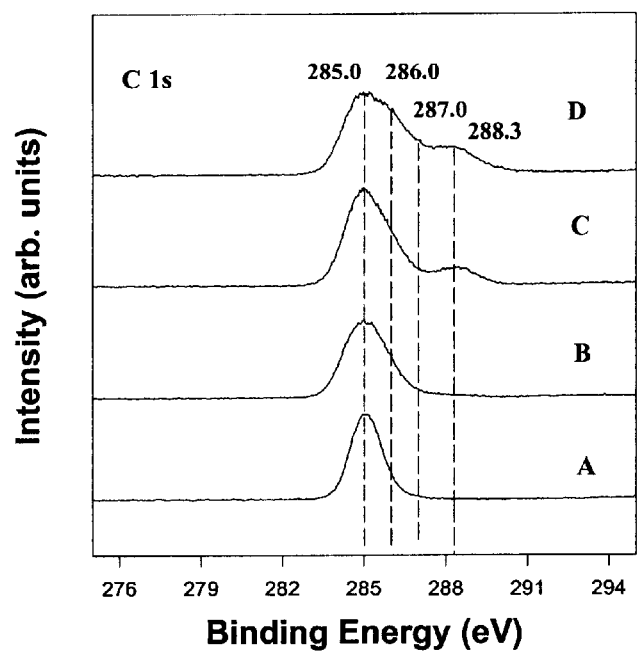
FIG. 7B shows C(1s) and FIG. 7C shows N(1s) core level x-ray photoelectron spectra of blank silicone (A), APTES layer on silicone (B), maleimide layer (C) and peptide layer (D).
Figure 7C:
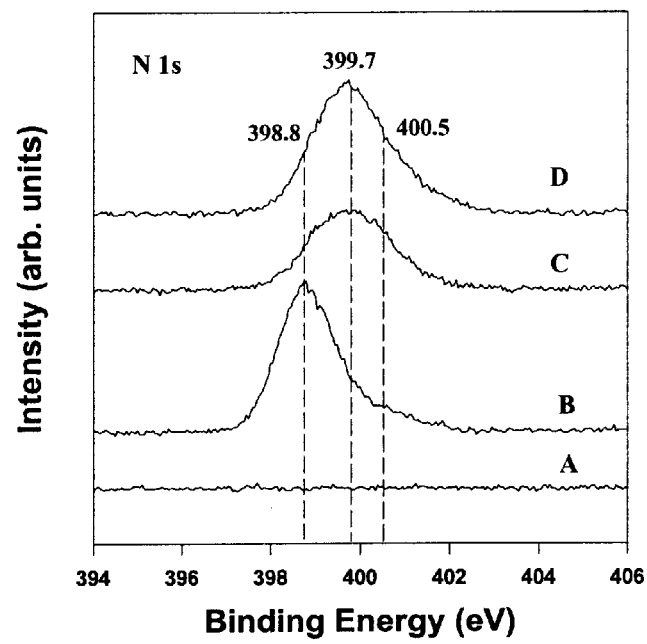

Covalent attachment of peptides to the silicone surfaces are used, as described above and depicted schematically in FIG. 7A. The GRGDSP (SEQ ID NO:1) peptide sequence is known to activate the integrin binding mechanism of various cell lines (Xiao et al., *Langmuir* 14: 5507–5516, 1998). The peptide functionalized silicone membranes were characterized by radiolabelling and x-ray photoelectron spectroscopy. $^{125}$I radiolabelling of the peptide was performed, then the peptide was bound to the silicone surface. FIG. 7B shows the I) C(1s) and II) N(1s) core level x-ray photoelectron spectra for the silicone surfaces at various stages of preparation (letters on spectra correspond to those in FIG. 7A). The appearance of new C(1s) components and the shift in the N(1s) peaks are both consistent with the chemistry depicted in FIG. 7A.

Figure 8:
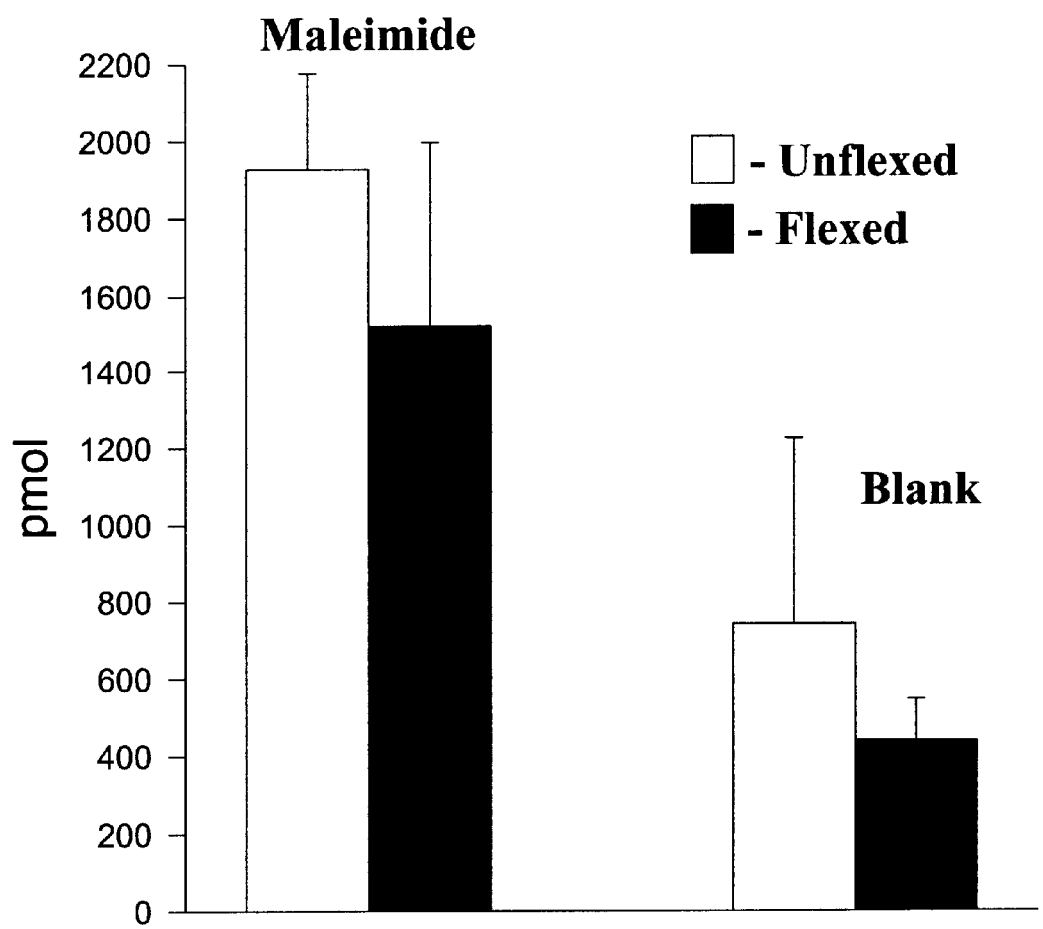
FIG. 8 shows the results of flexing of the iodinated peptide modified silicone membranes for 48 hrs under cell culture media. 79% of the covalently bound peptide (Maleimide) and 59% of the non-covalently bound peptide (Blank) remain on the surface following flexing.

The $^{125}$I-peptide functionalized silicone membranes were flexed in a Flexercell apparatus for 48 hours under cell growth media. The results of this experiments are shown in FIG. 8. Greater than 75% of the covalently bound peptide (labeled "Maleimide") remained bound to the surface after flexing. By contrast, only about 60% of the noncovalently bound peptide (labeled "Blank") remains on the silicone surface after similar flexing experiments. The binding of the peptide layer after flexing in vitro is examined in the present Example because the first step used by other researchers—oxygen plasma treatment (as opposed to water plasma treatment employed here)—leads to the formation of a loosely bound silica layer that is poorly coupled to the bulk silicone (Bowdin et al., *Appl. Phys. Lett.* 75: 2557–2559, 1999). It is generally known that silica films formed on polymers can crack or delaminate upon flexing (Yanaka et al., *J. Appl. Phys.* 90: 713–719, 2001). By contrast, the water plasma treatment utilized in the present invention simply modifies the silicone with OH groups, rather than depositing a stiff silica film. This ameliorates the problems of cracking and delamination seen membranes which have silica films formed on polymers. Thus, the membranes described in the present invention are a significant improvement over those available to those of skill in the art.

Figure 9:
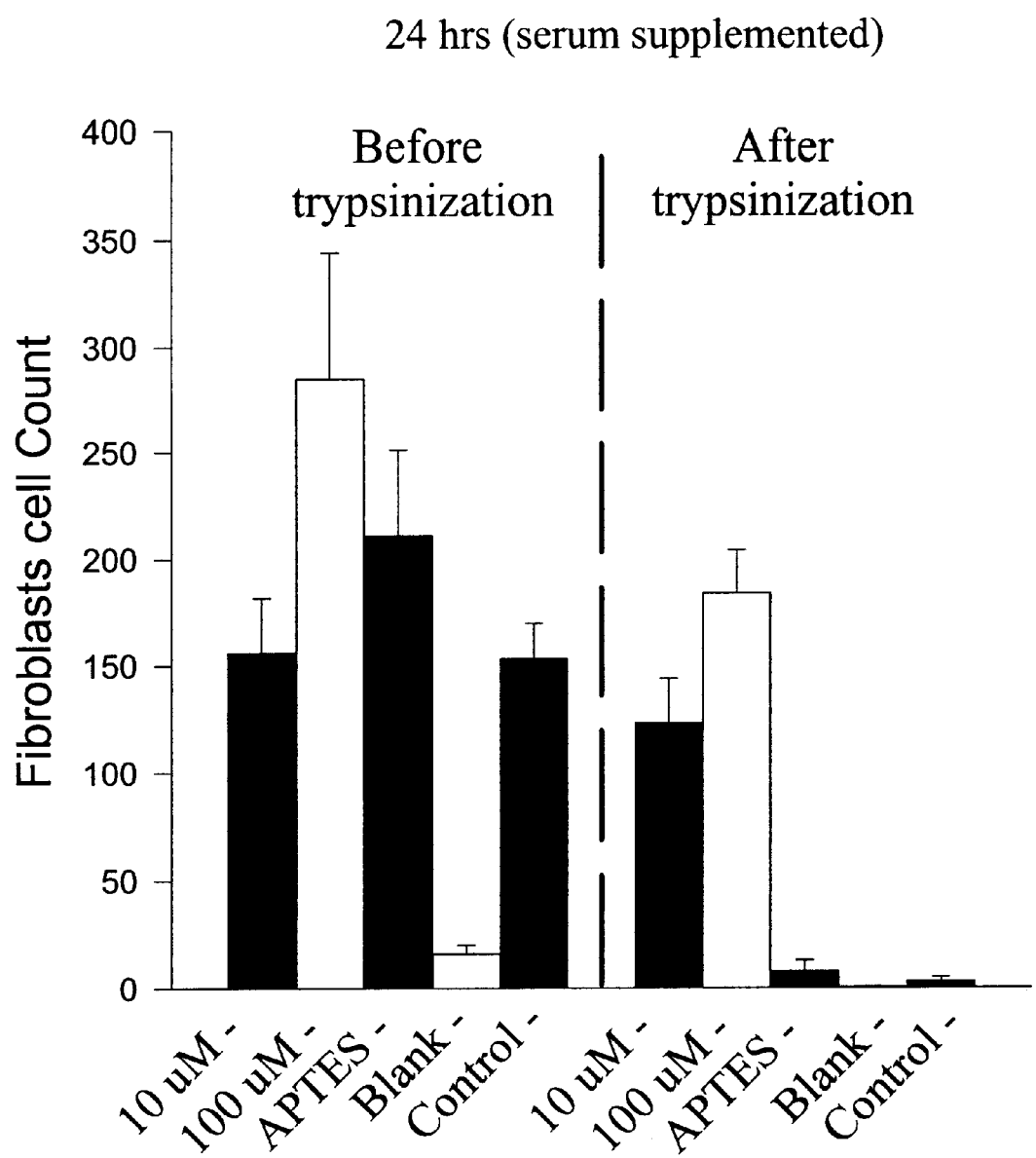
FIG. 9 shows the fibroblast cell count on blank, APTES, and peptide modified (10 and 100 µM) silicone membranes. Cell count shown before (left) and after trypsinization. Only the peptide surfaces show high cell counts after trypsinization. The control is tissue culture polystyrene control. 10 and 100 µM refer to the input concentration of the peptide solutions used to prepare the membranes.

FIG. 9 shows the results of rat cardiac fibroblasts grown on the various chemically modified and blank silicone membranes. Both the peptide concentrations (labeled "10 μM" and "100 μM" and the amine surface (labeled "APTES") demonstrated enhanced cell numbers compared to the blank silicone after 24 hours. After trypsin washing, used to remove bound fibroblasts, only the peptides displayed enhanced cell binding compared to both blank silicone and the tissue culture polystyrene control. These results demonstrate that these peptide functionalized silicone surfaces enhance cell binding.

Example 4

Dynamic Mechanical Pacing of Cardiac Myocytes

This example is directed to mechanically deforming cardiac cells attached to traditional surfaces. The surface on which cells are grown greatly affects both the plating efficiency and the long-term attachment during mechanical manipulation. The best attachment of cardiomyocytes is on commercial plastic Petri dishes coated with Type I collagen (68±4%, n=6) but these are rigid so that cells cannot be moved on them. The collagen-coated elastic membranes that came with the original Flexercell FX-2000 System (Flex-1 plates) are acceptable (58±8% of plated cells attach, n=10) but collagen-coated membranes provided with the new FX-3000 System (Bioflex plates) only allow a small and variable fraction of plated cells to adhere (38±12%, n=8). These initial numbers of cells are even further reduced as soon as any mechanical manipulation is performed on the Bioflex membranes. These results were particularly disappointing, as the Flexercell FX3000 System provides a convenient method to subject cultured monolayers to either static or cyclic, uniform radial strain, an important factor that is not achievable with the older FX-2000 System. Of course, neither commercially available system provides microtextured membranes with chemically modified surfaces to which ligand peptides are covalently attached. The many shortcomings of these commercially available systems have thus stimulated the use of a variety of "home-made" stretching devices. Some details relevant to this application are briefly outlined below.

Static Stretch of Aligned Cultures

The lengths and widths of myocytes maintained at 10% stretch for 6 hours are measured. Unstretched aligned cells grown on parallel streaked collagen (Simpson et al., *J Cell Physiol* 161(1):89–105, 1994) are highly polarized with a length/width (L/W) ratio of 13.4±0.8 compared to randomly-oriented controls where L/W is 4.2±0.4 (n=4, P<0.001). Aligned cells stretched 10% are even more polarized with L/W ratio of 22.6±2.9 (n=4, P<0.03). In addition, the cell nucleus is distorted by stretching of the aligned cells with L/W nuclear ratio increasing from 1.8±0.2 to 2.6±0.2 upon 10% stretch (n=4, P<0.02). Nuclei of randomly oriented cells are more circular (1.3±0.05). Therefore, it appears that stretch and alignment affect the shape of both the nucleus and the cell (Heidkamp and Russell, *Cell Tissue Research*, 305:1221–127, 2001).

Static Stretch of Randomly Oriented Neonatal Myocytes Prolongs Myofibrillar Protein Half-life The inventors have demonstrated that intrinsic mechanical load in the form of spontaneous contractile activity increases the rate of myofibrillar protein synthesis, and reduces the susceptibility of contractile proteins to intracellular proteolysis (Samarel and Engelmann, *Am J. Physiol* 261, H1067–77, 1991; Samarel et al., *Am J Physiol* 263, C642–52, 1992; Sharp et al., *Circ.Res.* 73: 172–183, 1993; Byron et al., *Am J Physiol* 271, C01447–56, 1996). The relationship between external mechanical load (i.e. a 5% static stretch) and myofibrillar protein degradative rates is explored in the same model system (Simpson et al., *Am J Physiol* 270, C1075–87, 1996.) Spontaneously contracting, randomly oriented myocytes that were grown on collagen-coated silastic membranes were maintained under control conditions, or subjected to 5% linear stretch. Paired cultures were maintained in serum-free medium containing nifedipine (12 μm) to inhibit spontaneous contractions. Myofibrillar structure was evaluated by confocal and electron microscopy. Myofibrillar protein content and degradation were assessed by SDS-PAGE and by pulse-chase biosynthetic labeling experiments, respectively. Pulse-chase experiments revealed that contractile arrest accelerated the loss of protein-bound tracer from the total myofibrillar fraction, and from pre-labeled MyHC and actin, but not desmin. Sarcomeric disassembly developed in parallel with these metabolic changes. A 5% static load partially stabilized myofibrillar structure in nonbeating cells, and suppressed the loss of isotopic tracer from the total myofibrillar fraction, MyHC and actin in both beating and nonbeating cells. Contractile activity and/or static stretch promoted the accumulation of MyHC, actin and desmin. Applying a static load to myocytes that lacked pre-existing myofibrils did not promote the assembly of sarcomeres or alter protein turnover. These data indicate that rates of myofibrillar protein turnover are correlated with the organizational state of the sarcomere, and that contractile protein half-life can be prolonged by both intrinsic and extrinsic mechanical load. Static stretch increases MyHC half-life in contracting and nifedipine arrested myocytes. Randomly oriented, spontaneously contracting cells grown on collagen-coated silastic membranes were subjected to maintenance cultures, or 5% linear stretch. Paired membranes were maintained in medium containing nifedipine (12 μm) to inhibit spontaneous calcium transient and beating. MyHC half-life was determined by pulse-chase biosynthetic labeling.

Cyclic Stretch Induces Myocyte Hypertrophy and Altered Gene Expression

The inventors examined whether extrinsic mechanical load in the form of cyclic stretch induced myocyte hypertrophy, and led to down-regulation of contractile and calcium handling genes which have been associated with the remodeled, failing cardiac myocyte in vivo (Cadre et al., *J. Mol. Cell. Cardiol.* 30;2247–2259, 1998). Randomly aligned neonatal myocytes were maintained in serum-free culture medium under control conditions, or subjected to cyclic mechanical deformation (1.0 Hz, 20% maximal strain, 48 h) using the Flexercell FX-2000 System. Under these conditions, cyclic stretch induced hypertrophy, as evidenced by significant increases in total protein/DNA ratio, MyHC content, and ANF secretion. A similar approach may be used in analyzing gene expression changes associated with various mechanical deformations in the new myocyte culture system.

Cyclic Stretch-induced Alterations in MyHC and ANF mRNAs

Neonatal rat ventricular myocyte cultures were maintained under control conditions, or subject to cyclic stretch (48 h, 1 Hz, 20% maximal strain). Total RNA was isolated, size-fractioned, and transferred to nylon membrane. Northern blots were sequentially probed with $^{32}$P-labeled oligodeoxynucleotide or cDNA probes specific for αMyHC, β MyHC, ANF and GAPDH mRNAs, and 18S rRNA). Probe binding was detected by autoradiography, and quantified by scintillation spectroscopy.

Cyclic Stretch-induced FAK Phosphorylation

The signal transduction pathways that may be responsible for cyclic stretch-induced cardiac myocyte hypertrophy and altered gene expression are also being investigated. In recent studies, it has been found that focal adhesion kinase (FAK) a nonreceptor protein tyrosine kinase localized to cardiac myocyte focal adhesions and costameres is rapidly autophosphorylated in response to cyclic stretch. Focal adhesions may therefore serve to transmit mechanical deformations to the cell interior, as well as to provide a structural link between the ECM and the cardiac myocyte cytoskeleton. Of note, FAK activation has been implicated in both adhesion- and growth factor-induced cell signaling events leading to proliferation, differentiation and cell survival in other cell types. FAK activation also can indicate an acute pressure overload of the myocardium in vivo (Kuppuswamy et al., *J Biol Chem* 14;272(7):4500–8, 1997), and is a critically important component of endothelin-induced focal adhesion, costamere, and sarcomere assembly in vitro (Eble et al., *Am J Physiol Heart Circ Physiol.*, 278(5):H1695–H1707, 2000). Thus, these data indicate that mechanical deformation of cardiac myocytes elicits specific cell signaling events via integrins and focal adhesion proteins that may be critical to cardiac myocyte growth and differentiation. Similar studies are planned using microtextured membranes with covalently bonded peptide ligands to assess the degree and time course of FAK activation as compared to cells stretched on flat surfaces.

FAK phosphorylation is induced by cyclic stretch. Neonatal rat ventricular myocytes cultured in serum-free medium on Flex 1 plates for 48 h and then cyclically stretch (1 Hz, 30% maximal strain) for 2, 5, 15, and 30 min using a Flexercell apparatus. Tyrosine phosphorylated proteins were immunoprecipitated, size-fractionated by SDS-PAGE, and transferred to nitrocellulose membrane. Blots were probed with an anti-FAK polyclonal antibody and the protein bands were visualized using ECL. Cyclic stretch induces rapid FAK phosphorylation by 2 min.

Endothelin-induced FAK Phosphorylation in Myocytes Plated on Different Substrates Increased contractile activity (by endothelin) induces FAK phosphorylation. Neonatal rat ventricular myocytes were isolated and plated overnight at high density onto plastic dishes pre-coated with either collagen I (Col I), collagen IV (Col IV), fibronectin (FBN), laminin (LMN), or poly-L-lysine showing morphology and adherence of the cells. Half of the myocytes were subsequently stimulated with endothelin-1 (ET-1, 100 nM, 5 min), a potent agonist that stimulates focal adhesion formation and sarcomeric assembly. Cell extracts were then prepared from unstimulated [C] and ET-1 stimulated cells. Tyrosine phosphorylated proteins were immunoprecipatated, size-fractionated by SDS-PA GE, and transferred to nitrocellulose membrane. The resulting Western blot was probed with an anti-FAK polyclonal antibody and the protein bands were visualized using enhanced chemiluminescence. Note, ET-1 stimulated FAK phosphorylation in the myocytes plated on the Col I, Col IV and FBN pre-coated plates. FAK activation by ET-1 was less pronounced in cells maintained on laminin. No ET-1 induced FAK phosphorylation was observed on poly-L-lysine coated dishes.

Focal adhesion, costamere and sarcomere assembly can also be stimulated in low-density, noncontracting cardiomycotes by treatment with various neurohumoral agents (e.g. angiotensin II, phenylephrine, ET-1) that induce cardiomyocyte hypertrophy and remodeling in vivo. For instance, both phenylephrine (50 μM) (Eble et al., *Am. J. Physiol.* 274:C1226–C1237, 1998) and ET-1 (100 nM, 48 h) induce cardiomyocyte hypertrophy, as evidenced by increased total protein/DNA and MyHC/DNA ratios. Both agents also increase cell size, and stimulate the assembly of newly synthesized myofibrillar proteins into sarcomeres (Eble et al., *Am. J. Physiol.* 274:C1226–C1237, 1998; Eble et al., *Am J Physiol Heart Circ Physiol.*, 278(5):H1695–1707, 2000).

Endothelin-induced sarcomere assembly is associated with an increase in focal adhesion and costamere formation, and also an increase in the localization of phosphotyrosinated proteins into focal adhesions. Indeed, ET-1 causes the rapid tyrosine phosphorylation of both FAK and paxillin (Eble et al., *Am J Physiol Heart Circ Physiol.*, 278(5):H1695–H1707, 2000). Of particular interest is the intensity of both basal and agonist-induced FAK activation varies depending upon which ECM component the myocytes are attached to. In this case, static or cyclic stretch, rather than endothelin, is used to activate FAK. Different mechanical loading conditions can be tested, as well as different adhesive peptides and microtextures.

The new culture system is used to determine the limits of cell growth and mechanical signal transduction. Cardiac (high density, aligned, anatomically correct, physiologically functional) myocytes grown on microtextured peg and groove membranes will be maintained in the unstretched state (control). Cells will then be mechanically stimulated on the various microtextured and chemically bonded surfaces that have been generated.

In order to stress the cells, the inventors use three classes of mechanical distortions; namely (1) a single static stretch, (2) a staircase of small steps to mimic heart failure due to chronic increased diastolic volume, and (3) intermittent packets of activity to mimic exercise. The novel culture model provides the first opportunity to mimic physiological and patho-physiological conditions of the human heart.

(1) Sudden overload. The inventors apply a sudden length extension of 5, 10 or 20% in the direction parallel (longitudinal strain) or perpendicular (transverse strain) to the direction of the myofibrils. The inventors monitor rapid changes in phosphorylation of specific cell signaling proteins (FAK, paxillin, MAPK) over the time course from minutes to hours.

(2) Heart failure. The inventors use the dynamic strain system (Flexercell FX-3000) in order to deform the cells mechanically at a given amplitude and frequency. In this aspect the inventors use multiple small stretches (steps) of varying length. Time between incremental increases in stretch will start at 5% every 2 h, and then be varied to determine the amplitude and frequency of stepped increases that result in maximal protein content (protein/DNA ratio). This will reproduce the positive feedback circuit between load and mal-adaptation that plagues the failing heart.

(3) Exercise. Passive mechanical distortions to silastic microtextured membranes with a sine wave of 5% amplitude for 200 Hz frequency for one hour followed by a 2 h rest interval. This 3 h pattern is repeated for 48 hours with samples taken at 3, 6, 9, 24 and 48 h. These conditions are designed to mimic cyclic patterns during exercise training. This will help determine the role and rest intervals in cardiac physiological adaptation, compared with the response seen in heart failure.

Once this mechanical stimulation limit is determined, the inventors will again measure rates of protein accumulation, cell geometry and gene expression. The inventors will first examine the effects of the stepped stretch protocol on the synthesis, turnover and gene expression of contractile proteins, as compared to their nonstretched counterparts. Fractional synthetic rates (Ks, %/h) will be determined for MyHC and Kd values will be estimated in pulse-chase experiments. In addition, levels of mRNAs encoding genes up- or down-regulated during cardiac hemodynamic overload in vivo will be examined (Cadre et al., *J. Mol. Cell. Cardiol.* 30;2247–2259, 1998). Here the inventors select members of the major contractile proteins (actin, α-MyHC, β-MyHC), the calcium release and uptake system (SERCA2, RyR), and a key focal adhesion signaling protein (FAK). Also, there may be a degree of stretch in the step protocol that induces gene expression changes characteristic of heart failure in vivo.

The original Flexercell (FX2000) had opaque membranes that did not permit morphological studies. Nevertheless it had adhesive membranes. The new Flex3000 (Bioflex) allows excellent morphology because the membranes are transparent but in introducing this superior optical quality the adhesive properties were lost and the cells detach when mechanical deformed by the vacuum. Note that the Flexercell 3000 device imposes a radial stretching of the membranes as it stretches the circular membrane over the edge of the piston. The cells in the present invention are oriented in parallel arrays. This means that the cells on the 12 to 6 O'clock axis are stretched longitudinally, whereas the cells on the 3 to 9 O'clock axis are stretched transversely. This would be a big problem for any study that scraped the cells and looked at average data. However, many of the inventors' morphological methods retain information on individual cells so that the two axes can be analyzed separately from each membrane; one gives parallel strain and the other gives the perpendicular strain. The inventors contemplated production of membranes with concentric circles that would provide uniform transverse stretch if the myocytes would follow the circular grooves. Such membranes may be used once they have been down sized to the micro domain. Membranes that have radial spokes also may be fabricated that would allow longitudinal strain to be experienced by all myocytes. For single cell assay it is not an issue but for biochemical and molecular extraction methods where all cells are pooled, the inventors will use radial and concentric membranes.

The new microtextured surfaces will produce addition of new myofibrils reproducing the hypertrophy observed in response to both physiological and pathological stimuli. These experiments will help provide a better understanding of the mechanisms involved in pathogenesis of heart failure and normal adaption to exercise.

It will be clear that the invention may be practiced otherwise than as particularly described in the foregoing description and examples. Incorporated herein by reference is Deutsch et al., *J. Biomed. Mater. Res. (Appl. Biomater)* 53:267–275, 2000, which provides additional methods that may be useful in conjunction with the present invention.

Example 5

The Membranes of the Present Invention May be Used in Contact Inhibition Investigations Most normal cells and many cell lines do not grow indefinitely in the body or in culture, rather they are inhibited by contact with their neighbors; this state of arrest is known as contact inhibition. For example, melanoma cell lines can be cultured under conditions where they become inhibited by contact (Valyi-Nagy et al., 1993, *Int. J. Cancer* 54:159–165), as can neural precursor lines transformed by polyoma large tumor (T) gene (Galiana et al., 1995, *Proc. Natl. Acad. Sci. U.S.A.* 92:1560–1564), derivatives of colon HT29 cells (Velcich et al., 1995, *Cell Growth Differ.* 6:749–757), human umbilical vein endothelial cells (Gaits et al., *Biochem. J.* 311:97–103, 1995), nonparenchymal epithelial cells (Johnson et al., *Cancer Lett.* 96:37–48, 1995), and many others.

In the past, the phenomenon of contact inhibition of cells has been used to select variants that continue to grow when saturation of the culture dish bottom has been reached. Foci have been isolated, comprised of cells that no longer respond to contact inhibitory signals and are often more likely to form tumors in animals than their parental counterparts. Indeed, the initial identification of cellular oncogenes involved such an experimental approach. Land et al., 1983, *Nature* 304:596–602; Copeland et al., 1979, *Cell* 17:993–1002.

In the present invention, the inventors have demonstrated that the membranes of the present invention can be used to model and study contact inhibition. Seeing as loss of growth regulation of cells, e.g., in cancer, is frequently reflected in the loss of contact inhibition of cell proliferation, such models and studies will be useful in elucidating the mechanisms of such a loss of inhibition as well as providing in vitro models which can be used to test various anti-cancer agents.

Figures 10A, 10B:
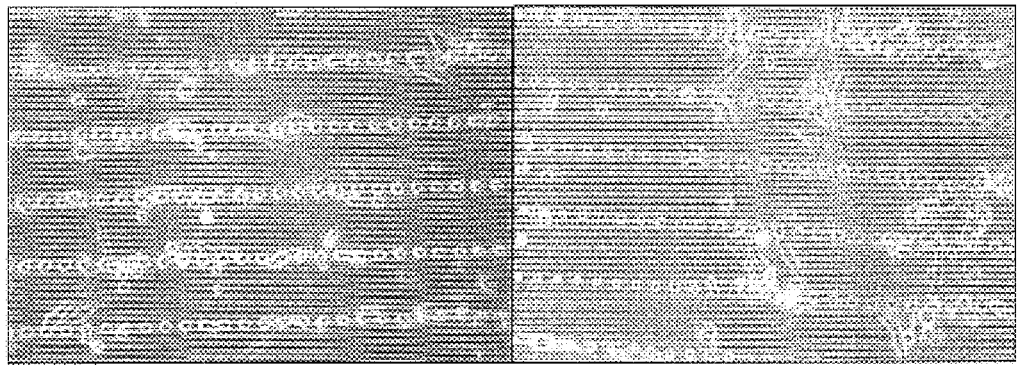
FIG. 10A–FIG. 10D shows phage images of cancer cell lines grown on 10 µm pegged silicone membranes.
Figures 10C, 10D:
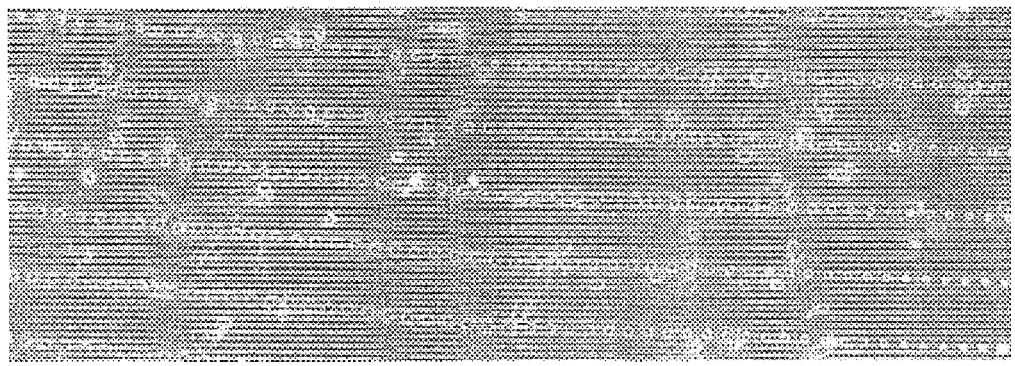

FIGS. 10A–D show phase images of cancer cell lines grown on 10 μM pegged silicone membranes and demonstrate that two kinds of cancer cells can be grown on the membranes of the present invention but that cell response depends on the inherent properties of the type of cancer. For example, a cell line (Mum-2) that was derived from highly metastatic (invasive) cells in vivo differed from the cells derived from a solid tumor (Mel-1). FIG. 10A and 10B show non aggressive Mel-1 cells which appear to attach to the pegs and cluster around the pegs. FIG. 10C and 10D show the aggressive Mum-2 cells which appear to ignore the pegs and spread to distant locations on the membranes.

Figures 11A, 11B:
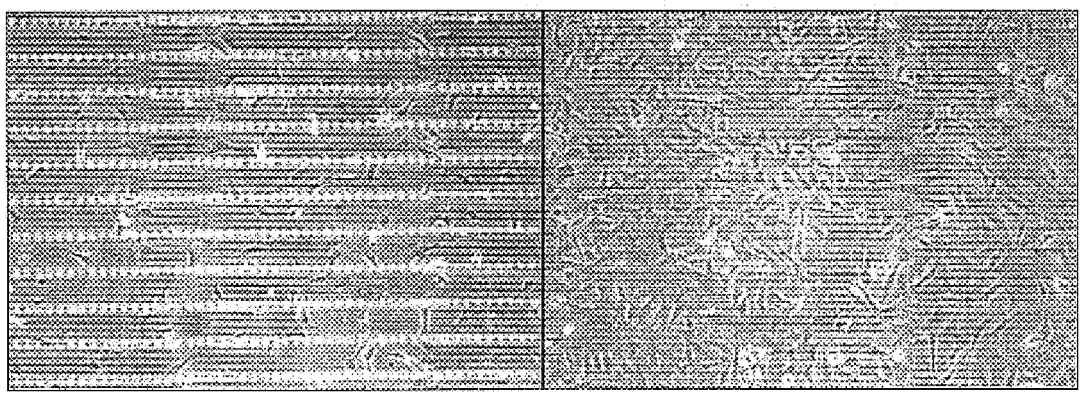
FIG. 11A and FIG. 11B show fibroblast proliferation on 10 µM pegged and flat silicone membranes, respectively, as observed on day 5 of growth.
Figure 12:
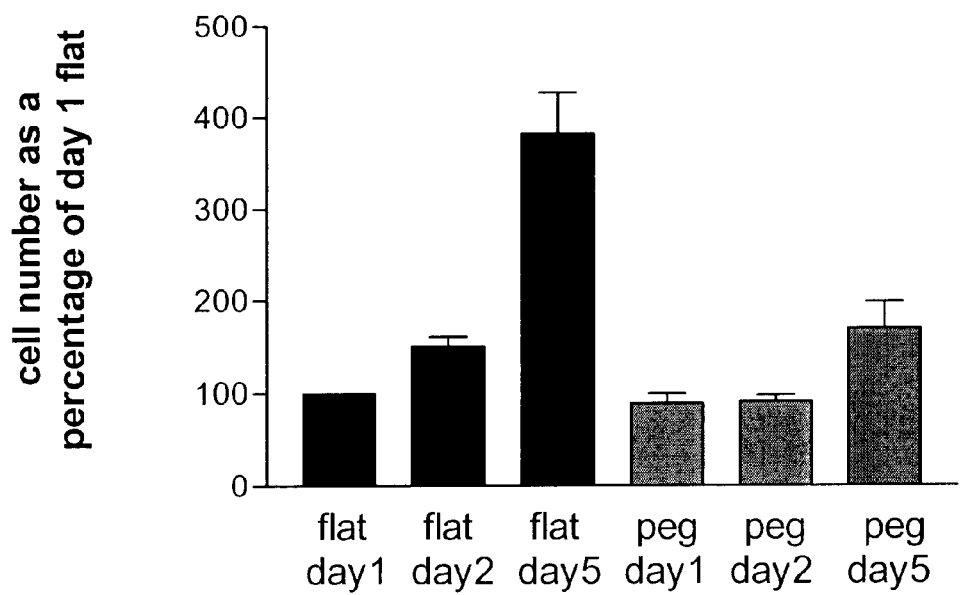
FIG. 12 shows cardiac fibroblast cell proliferation on flat and 10 µM pegged silicone membranes.

In order to demonstrate that cells grown on the membranes of the present invention undergo contact inhibition more than cells grown on conventional flat surfaces, the inventors seeded fibroblasts on pegged and flat silicon membranes and also on the microtextured membranes of the present invention. For determining the degree of cell attachment to 10 μm pegs, fibroblast cells were cultured in Dulbecco's Modified Eagle's medium with L-glutamine from the first passage of the primary myocyte culture. Fibroblasts were plated at 20 cells per $mm^2$ and total cell number was counted after trypsinisation over a 5 day period. In FIG. 11, fibroblast proliferation on 10 μM pegged (FIG. 11A) and flat silicone membranes (FIG. 11B) is depicted at 5 days of growth. These figures demonstrates the ability of the fibroblasts to exhibit reduced proliferation and growth (as indicated by increased cell number of cells seeded on the pegged membranes as compared to the flat membrane) and also demonstrates the tendency of the fibroblasts to extend filopedia towards and attachment to the pegs. The finding that the growth of fibroblasts on microtextured silicone membrane is greatly reduced is shown in FIG. 12. Cell division was assessed by counting the number of cells per dish and expressing this number as a percentage of the number of cells on a flat silcone surface. FIG. 12 shows fibroblast cell proliferation per dish over a 5 day period.

Note that at 5 days of culture, fibroblast cell growth was 2 fold higher on flat membranes compared with pegged ($p<0.005$ n=6 cultures).

Figure 13:
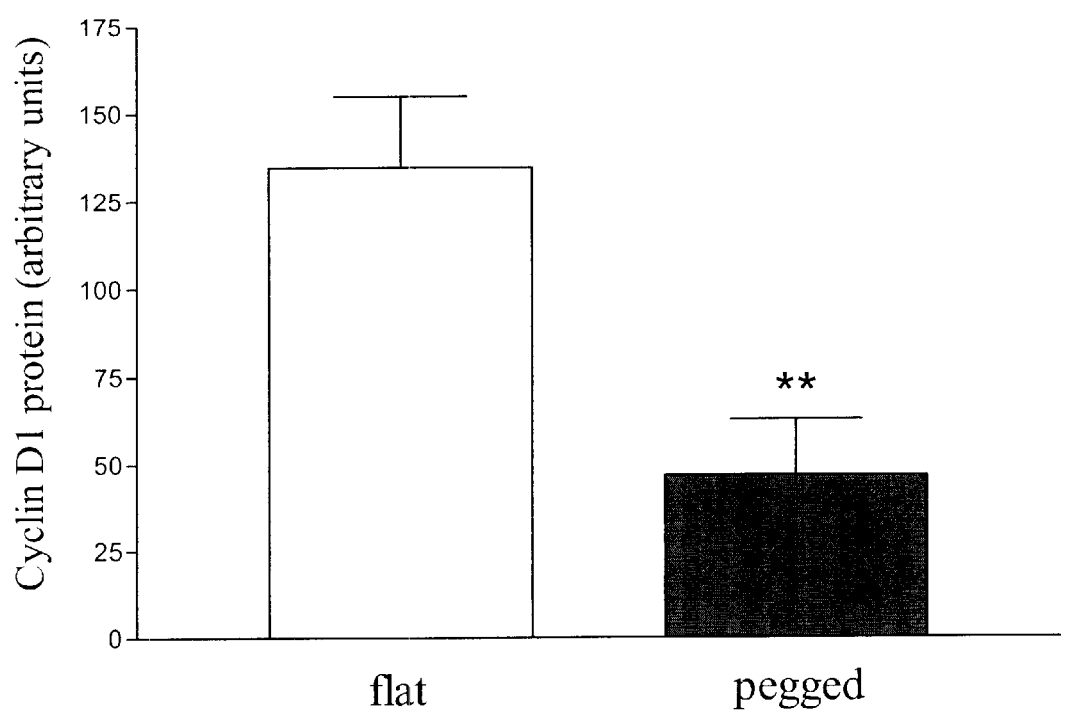
FIG. 13. Cyclin D1 protein expression in cardiac fibroblasts cultured on flat and pegged silicone membranes. Cyclin D1 protein is significantly reduced in cardiac fibroblasts cultured on pegged membranes compared with flat. Actin protein, not shown, remained unchanged.

FIG. 13 shows a Western blot of Cyclin D chosen as an indicator of the state of the cell cycle with respect to cell division. FIG. 13 shows that cyclin D1 is 2.8 fold higher and significantly different ($p<0.01$) in fibroblast cultures grown on flat membranes after 48 hours of culture compared with 10 micron pegged membranes. This shows that the peg micro-topography alone blocks cell division by contact inhibition. This is in contrast to the conclusions reached by other researchers' studies which employed positive pegs and negative holes to observe fibroblast proliferation (Green et al., *J Biomed Mater Res.*, 28(5)647–53, 1994). Green et al. found fluctuations between the flat, pegged and pitted surfaces analyzed over a 12 day period, but these fluctuations seemed to indicate that the flat surface was consistently in the middle of the surfaces analyzed. The data of Green et al. are most likely explained by the fact that the projections and pits employed in that study are closer to each other than those of the present invention and as such the cells "see" those projections and pits as a flat surface.

The inventors found that fibroblast proliferation is decreased on the microtextured surface(s) of the present invention has several potential implications. Current cell cultures are often overgrown with fibroblasts, a fact that may obscure potentially significant experimental findings, by inundating cultures with fibroblast expression levels and not that of the particular cell of interest; the cardiac contractile myocyte. By culturing the targeted cell on microtextured surfaces, this "contamination", can be reduced significantly, thereby allowing any data acquired from such a culture to closer approximate what is occurring in, and representative of, the targeted contractile cell type.

Additionally, the microtextured surface of the present invention will be an invaluable tool in elucidating the signaling pathways and the mechanisms responsible for the phenomenon of contact inhibition. As a complement to this potential for studies on contact inhibition, the inventors envision the use of the surfaces of the present invention in efficient and quick screening procedures for cell biopsies of diseased cell states that feature contact inhibition as one of their characteristics. Furthermore, the surfaces could prove invaluable in differentiating among cell types within a more broadly defined group of cells, such as cancer cells, by allowing rapid and efficient determination of which cancers are more likely to behave aggressively. This has already been demonstrated in the cancerous cell lines depicted in FIGS. 10A–10D.

Numerous modifications and variations of the present invention are possible in light of the above teachings and, therefore, are within the scope of the invention. The entire disclosure of all publications cited herein are hereby incorporated by reference.

We claim:

1. A biocompatible, deformable membrane for the growth of cells comprising a microtextured polymer membrane having planar surface, said microtextured polymer membrane comprising projections extending perpendicular to said planar surface, said projections having a size of between 1 μm to 15 μm; and longitudinal grooves in the planar surface;

wherein said polymer membrane comprises a surface modification to facilitate cellular adhesion to said membrane, and further wherein said growth of said cells on said membrane provides enhanced cellular differentiation of said cells as compared to growth on said polymer membrane in the absence of said grooves and/or said projections.

2. The membrane of claim 1, wherein said polymer membrane is made from a material selected from the group consisting of silicone, hydrogels, and biodegradable polymers.

3. The membrane of claim 1, wherein said surface modification comprises laminin, fibronectin, partial peptide sequences thereof or modifications of laminin or fibronectin.

4. The membrane of claim 1, wherein said cells are muscle cells and the growth of said muscle cells on said membrane produces muscle cells that have contractile function.

5. A membrane of claim 1, wherein said membrane is fabricated into a master wafer using a method selected from the group consisting of photolithography, diamond turning, diamond ruling and laser machining.

6. The biocompatible, deformable membrane claim 1, wherein said projections have a size of 5 μm.

7. The biocompatible, deformable membrane of claim 1, wherein said projections have a size of 10 μm.

8. The biocompatible, deformable membrane of claim 1, wherein said surface modification comprises a fibronectin receptor ligand GRGDSP (SEQ ID NQ:1) covalently bound to the surface of the membrane.

9. The biocompatible, deformable membrane of claim 1, wherein said surface modification comprises the laminin receptor ligand YIGSR (SEQ ID) NO:2) covalently bound to the surface of the membrane.

10. The biocompatible, deformable membrane of claim 8, wherein said surface modification further comprises the laminin receptor ligand YIGSRC (SEQ ID NQ:2) covalently bound to the surface of the membrane.

11. The compatible deformable membrane of claim 2, wherein said biodegradable polymer is bioerodible.

12. A method of growing muscle cells comprising contacting muscle cells with the membrane of claim 1, under media conditions suitable to facilitate the growth of said muscle cells wherein growth of said muscle cells on said membrane reproduces the physiological micro-architecture of said muscle cells.

13. The method of claim 12, wherein said muscle cells are myocardial cells.

14. The method of claim 12, wherein said muscle cells grown on said membrane are responsive to neurohormonal stimulation.

15. The method of claim 12, wherein said muscle cells grown on said membrane exhibit contractile function that mimic the contractile function of the muscle cell in vivo, wherein said cells have mechanical deformation properties that are similar to the mechanical deformation properties of said cells in vivo.

16. A method of producing a tissue patch comprising:
    (a) providing cells;
    (b) contacting said cells with the membrane of claim 1;
    (c) growing said cells in culture to allow the formation from said cells.

17. The method of claim 16, wherein said cells are selected from the group consisting of skeletal muscle cells, smooth muscle cells, cardiac muscle cells, vascular endothelial cells, lymphatic endothelial cells, stem cells, endothelial cartilage cells, and bone cells.

* * * * *

UNITED STATES PATENT AND TRADEMARK OFFICE
CERTIFICATE OF CORRECTION

PATENT NO. : 6,942,873 B2
DATED : September 13, 2005
INVENTOR(S) : Brenda Russell et al.

It is certified that error appears in the above-identified patent and that said Letters Patent is hereby corrected as shown below:

<u>Column 1,</u>
Line 9, insert -- This invention was made with government support under grants HL040880, HL064956, and HL062426 awarded by the National Institutes of Health. The government has certain rights in the invention. --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,942,873 B2 Page 1 of 1
APPLICATION NO. : 09/961834
DATED : September 13, 2005
INVENTOR(S) : Brenda Russell et al.

It is certified that error appears in the above-identified patent and that said Letters Patent is hereby corrected as shown below:

In the Claims:

At Column 37, line 4, "having planar" should be -- having a planar --.

At Column 37, line 31, "membrane claim" should be -- membrane of claim --.

At Column 38, line 3, "YIGSR" should be --YIGSRC --.

At Column 38, line 3, "ID) NO" should be -- ID NO --.

At Column 38, line 7, "NQ:2" should be -- NO:2 --.

At Column 38, line 31, "from" should be -- of tissue from --.

Signed and Sealed this

Tenth Day of April, 2007

JON W. DUDAS
*Director of the United States Patent and Trademark Office*